United States Patent [19]

Kleemann et al.

[11] Patent Number: 5,753,710
[45] Date of Patent: May 19, 1998

[54] SUBSTITUTED BENZYLOXYCARBONYLGUANIDINES, A PROCESS FOR THEIR PREPARATION, THEIR USE AS A MEDICAMENT OR DIAGNOSTIC, AND A MEDICAMENT CONTAINING THEM

[75] Inventors: Heinz-Werner Kleemann, Bischofsheim; Joachim Brendel, Bad Vilbel; Jan-Robert Schwark, Frankfurt; Andreas Weichert, Egelsbach; Hans-Jochen Lang, Hofheim; Udo Albus, Florstadt; Wolfgang Scholz, Eschborn, all of Germany

[73] Assignee: Hoechst Aktiengesellschaft, Frankfurt am Main, Germany

[21] Appl. No.: 648,499

[22] Filed: May 15, 1996

[30] Foreign Application Priority Data

May 17, 1995 [DE] Germany ............... 195 18 073.9

[51] Int. Cl.⁶ ............... A61K 31/155; C07C 279/10
[52] U.S. Cl. ............... 514/634; 564/237; 564/85; 514/311; 514/357; 514/603; 546/152; 546/332
[58] Field of Search ............... 560/159, 158; 514/331, 311, 357, 603, 634; 546/152, 332; 564/85, 237

[56] References Cited

U.S. PATENT DOCUMENTS

| 2,734,904 | 2/1956 | Burtner ............... 260/295 |
| 5,091,394 | 2/1992 | Englert et al. ............... 514/331 |
| 5,292,755 | 3/1994 | Englert et al. ............... 514/331 |

FOREIGN PATENT DOCUMENTS

| 844 832 | 2/1977 | Belgium . |
| 0 416 499 | 3/1991 | European Pat. Off. . |
| 0 612 723 | 8/1994 | European Pat. Off. . |
| 0 640 588 | 3/1995 | European Pat. Off. . |

OTHER PUBLICATIONS

Krug and Nowak: Pochodne Gwanidyny II Nowe Metody Otrzymywania Nicktorych Acylolochod–nych Guanidyny; Roczniki Chemii. vol. 41. pp. 1087–1091, 1967.
Rempp Chemie Lexikori: pp. 579 and 391.
See the Search Report, Examples 5 Abstract.
Scholz, W. et al.: Hoe 694, a new $Na^+/H^+$ exchange inhibitor and its effects in cardiac Ischaemia Br. J. Pharmacol. 109:582–568, 1993.
Derwent Abstract of EP 0 612 723.
Derwent Abstract of EP 0 416 489.
Derwent Abstract of EP 0 640 588.
Derwent Abstract of BE 844 832.

*Primary Examiner*—C. Warren Ivy
*Assistant Examiner*—Charanjit S. Aulakh
*Attorney, Agent, or Firm*—Finnegan, Henderson, Farabow, Garrett & Dunner, L.L.P.

[57] ABSTRACT

Substituted benzyloxycarbonylguanidines, a process for their preparation, their use as a medicament or diagnostic, and a medicament containing them. There are described compounds of the formula I

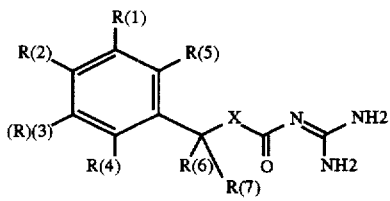

in which the substituents R(1) to R(7) and X have the meanings shown in the claims, and their pharmaceutically tolerable salts. These are effective inhibitors of the cellular sodium proton antiporter ($Na^+/H^+$ exchanger). They are therefore outstandingly suitable for the treatment of all diseases which can be attributed to increased $Na^+/H^+$ exchange.

19 Claims, No Drawings

SUBSTITUTED BENZYLOXYCARBONYLGUANIDINES, A PROCESS FOR THEIR PREPARATION, THEIR USE AS A MEDICAMENT OR DIAGNOSTIC, AND A MEDICAMENT CONTAINING THEM

DESCRIPTION

This invention relates to substituted benzyloxycarbonylguanidines, a process for their preparation, their use as a medicament or diagnostic, and a medicament containing them.

More particularly, an embodiment of the invention relates to benzyloxycarbonylguanidines of the formula I

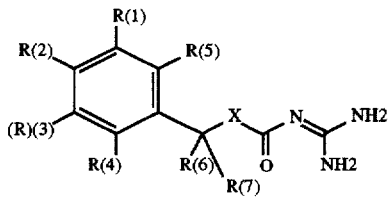

in which:

- R(1), R(2) and R(3) independently of one another are —Y—{4—R(8)-phenyl},
  —Y—{3—R(8)-phenyl} or —Y—{2—R(8)-phenyl}, where the phenyl in each case is unsubstituted or substituted by 1–2 substituents selected from the group consisting of F, Cl, —CF$_3$, methyl, hydroxyl, methoxy and —NR(96)R(97); R(96) and R(97) independently of one another are hydrogen or —CH$_3$;
  Y is a bond, CH$_2$, oxygen, —S— or —NR(9); R(9) is hydrogen or alkyl having 1, 2, 3 or 4 carbon atoms;
  R(8) is SO$_a${NR(98)}$_b$NR(99)R(10);
  a is 1 or 2;
  b is 0 or 1;
  a+b=2;
  R(98), R(99) and R(10) independently of one another are hydrogen, —(C$_1$-C$_8$)-alkyl, benzyl, —(C$_2$-C$_8$)-alkylene—NR(11)R(12), (C$_2$-C$_8$)-alkylene—NR(13)—(C$_2$-C$_8$)-alkylene—NR(37)R(38) or (C$_0$-C$_8$)-alkylene—CR(39)R(40)—CR(41))R(42)(C$_0$-C$_8$)-alkylene—NR(43)R(44); R(11), R(12), R(13), R(37), R(38), R(43) or R(44) independently of one another are hydrogen, —(C$_1$-C$_8$)-alkyl or benzyl; R(39), R(40), R(41) and R(42) independently of one another are hydrogen, —(C$_1$-C$_8$)-alkyl or —(C$_0$-C$_3$)-alkylenephenyl, where the phenyl is unsubstituted or substituted by 1–3 substituents selected from the group consisting of F, Cl, —CF$_3$, methyl and methoxy;

or

- R(99) and R(10) together are 4–6 methylene groups, of which one CH$_2$ group can be replaced by oxygen, —S—, —NH—, —N—CH$_3$ or —N-benzyl;

or

- R(8) is SO$_a${NR(98)}$_b$NR(95)—C{═N—R(94)}—NR(93)R(92); R(92), R(93), R(94) and R(95) independently of one another are hydrogen or alkyl having 1, 2, 3 or 4 carbon atoms;

or

- R(1), R(2) and R(3) independently of one another are pyrrol-1-yl, pyrrol-2-yl or pyrrol-3-yl, which is unsubstituted or substituted by 1–4 substituents selected from the group consisting of F, Cl, Br, I, —CN, (C$_2$-C$_8$)-alkanoyl, (C$_2$-C$_8$)-alkoxycarbonyl, formyl, carboxyl, —CF$_3$, methyl, and methoxy;

or

- R(1), R(2) and R(3) independently of one another are hydrogen, —(C$_1$-C$_8$)-alkyl, —(C$_2$-C$_8$)-alkenyl or —(CH$_2$)$_m$R(14);
  m is zero, 1 or 2;
  R(14) is —(C$_3$-C$_8$)-cycloalkyl or phenyl, which is unsubstituted or substituted by 1–3 substituents selected from the group consisting of F, Cl, —CF$_3$, methyl, methoxy and —NR(15)R(16); R(15) and R(16) are hydrogen or —CH$_3$;

or

- R(1), R(2) and R(3) independently of one another are —Q—4—{(CH$_2$)$_k$—CHR(17)—(C═O)R(20)}-phenyl, —Q—3—(CH$_2$)$_k$—CHR(17)—(C═O)nm R(20)}-phenyl or —Q—2—{(CH$_2$)$_k$—CHR(17)—(C═O)R(20)}-phenyl, where the phenyl in each case is unsubstituted or substituted by 1–2 substituents selected from the group consisting of F, Cl, —CF$_3$, methyl, hydroxyl, methoxy and —NR(35)R(36); R(35) and R(36) independently of one another are hydrogen or —CH$_3$;
  Q is a bond, oxygen, —S— or —NR(18); R(18) is hydrogen or —(C$_1$-C$_4$)-alkyl;
  R(17) is —OR(21) or —NR(21)R(22); R(21) and R(22) independently of one another are hydrogen, —(C$_1$-C$_8$)-alkyl, —(C$_1$-C$_8$)-alkanoyl, —(C$_1$-C$_8$)-alkoxycarbonyl, benzyl, benzyloxycarbonyl;

or

- R(21) is trityl;
  R(20) is —OR(23) or —NR(23)R(24); R(23), R(24) independently of one another are hydrogen, —(C$_1$-C$_8$)-alkyl or benzyl;
  k is zero, 1, 2, 3 or 4.

or

- R(1), R(2) and R(3) independently of one another are (C$_1$-C$_9$)-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino;

or

- R(1), R(2) and R(3) are —SR(25), —OR(25), —NR(25)R(26), —CR(25)R(26)R(27);
  R(25) is —C$_f$H$_{2f}$—(C$_1$-C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
  f is zero, 1 or 2;
  R(26) and R(27) independently of one another are defined as R(25) or are hydrogen or (C$_1$-C$_4$)-alkyl;

or

- R(1), R(2) and R(3) independently of one another are (C$_1$-C$_9$)-heteroaryl N-oxide, which is linked via C or N and which is unsubstituted or substituted by 1–3 substituents selected from the group consisting of F, Cl, CF$_3$, CH$_3$, methoxy, hydroxyl, amino, methylamino and dimethylamino:

or

- R(1), R(2) and R(3) independently of one another are —SR(28), —OR(28), —NR(28)R(29) or —CR(28)R(29)R(30);
  R(28) is —C$_g$H$_{2g}$—(C$_1$-C$_9$)-heteroaryl N-oxide, which is unsubstituted or substituted by 1–3 substituents selected from the group consisting of F, Cl, CF$_3$, CH$_3$, methoxy, hydroxyl, amino, methylamino and dimethylamino;

g is zero, 1 or 2;

R(29), R(30) independently of one another are defined as R(28), or are hydrogen or $(C_1-C_4)$-alkyl;

or

R(1), R(2) and R(3) independently of one another are hydrogen, F, Cl, Br, I, —C≡N, T—$(CH_2)_h$—$(C_iF_{2i+1})$, R(31)$SO_l$—, R(32)R(33)N—CO—, R(34)—CO— or R(45)R(46)N—$SO_2$, where the perfluoroalkyl group is straight-chain or branched;

T is a bond, oxygen, —S— or —NR(47);

l is zero, 1 or 2;

h is zero, 1 or 2;

i is 1, 2, 3, 4, 5 or 6;

R(31), R(32), R(34) and R(45) independently of one another are —$(C_1-C_8)$-alkyl, —$(C_3-C_6)$-alkenyl, $(CH_2)_n$R(48) or —$CF_3$;

n is zero, 1, 2, 3 or 4;

R(47) is hydrogen or alkyl having 1,2 or 3 carbon atoms;

R(48) is —$(C_3-C_7)$-cycloalkyl or phenyl, which is unsubstituted or substituted by 1–3 substituents selected from the group consisting of F, Cl, —$CF_3$, methyl, methoxy and —NR(49)R(50);

R(49) and R(50) are hydrogen or alkyl having 1, 2, 3 or 4 carbon atoms;

or

R(32), R(34) and R(45) are hydrogen;

R(33) and R(46) independently of one another are hydrogen or alkyl having 1, 2, 3 or 4 carbon atoms;

or

R(32) and R(33) and also R(45) and R(46) together are 5 or 6 methylene groups, of which one $CH_2$ group can be replaced by oxygen, —S—, —NH—, —$NCH_3$ or —N-benzyl;

or

R(1), R(2) and R(3) independently of one another are R(51)—A—G—D—;

R(51) is a basic protonatable radical, i.e. an amino group —NR(52)R(53), an amidino group R(52)R(53)N—C{=N—R(54)}— or a guanidino group R(52)R(53)N—C{=N—R(54)}—NR(55)—;

R(52), R(53), R(54) and R(55) independently of one another are hydrogen or alkyl having 1, 2, 3 or 4 carbon atoms;

or

R(52) and R(53) are a group $C_\alpha H_{2\alpha}$;

α is 4, 5, 6 or 7;

where if α=5, 6 or 7, a carbon atom of the group $C_\alpha H_{2\alpha}$ can be replaced by a heteroatom group O, $SO_d$ or NR(56), or R(53) and R(54) or R(54) and R(55) or R(52) and R(55) are a group $C_\gamma H_{2\gamma}$;

γ is 2, 3, 4 or 5;

where if γ=3, 4 or 5 a carbon atom of the group $C_\gamma H_{2\gamma}$ can be replaced by a heteroatom group O, $SO_d$ or NR(56);

d is zero, 1 or 2;

R(56) is hydrogen or methyl;

or

R(51) is a basic heteroaromatic ring system having 1–9 carbon atoms;

A is a group $C_e H_{2e}$;

e is zero, 1, 2, 3, 4, 5, 6, 7, 8, 9 or 10; where in the group $C_e H_{2e}$ a carbon atom can be replaced by one of the groups —O—, —CO—, —CH{OR(57)}—, $SO_r$—, —NR(57)—, —NR(57)—CO—, —NR(57)—CO—NH—, —NR(57)—CO—NH—$SO_2$— or —NR(57)—$SO_2$—;

r is zero, 1 or 2;

G is a phenylene radical

R(58) and R(59) independently of one another are hydrogen, methyl, methoxy, F, Cl, Br, I, $CF_3$ or —$SO_s$—R(60);

s is zero, 1 or 2;

R(60) is methyl or NR(61)R(62); R(61) and R(62) independently of one another are hydrogen or alkyl having 1, 2, 3 or 4 carbon atoms;

D is —$C_v H_{2v}$—$E_w$—;

v is zero, 1, 2, 3 or 4;

E is —O—, —CO—, —CH{OR(63)}—, —$SO_{aa}$— or —NR(63)—;

w is zero or 1;

aa is zero, 1 or 2 R(63) is hydrogen or methyl, or

R(1), R(2) and R(3) independently of one another are —$CF_2$R(64), —CF{R(65)}{R(66)}, —CF{$(CF_2)_q$—$CF_3$}{R(65)}, —C{$(CF_2)_p$—$CF_3$}=CR(65)R(66); R(64) is alkyl having 1, 2, 3 or 4 carbon atoms or cycloalkyl having 3, 4, 5, 6 or 7 carbon atoms; R(65) and R(66) independently of one another are hydrogen or alkyl having 1, 2, 3, or 4 carbon atoms;

q is zero, 1 or 2;

p is zero, 1 or 2;

or

R(1), R(2) and R(3) independently of one another are —OR(67) or —NR(67)R(68); R(67) and R(68) independently of one another are hydrogen or alkyl having 1, 2, 3, 4, 5 or 6 carbon atoms;

or

R(67) and R(68) together are 4, 5, 6 or 7 methylene groups, of which one $CH_2$ group can be replaced by oxygen, —S—, $SO_2$, —NH—, —$NCH_3$ or —N-benzyl;

R(4) and R(5) independently of one another are hydrogen, alkyl having 1, 2, 3 or 4 carbon atoms, F, Cl, —OR(69), —NR(70)R(71) or —$C_z F_{2z+1}$; R(69), R(70) and R(71) independently of one another are hydrogen or alkyl having 1, 2 or 3 carbon atoms;

z is 1, 2, 3 or 4;

R(6) and R(7) independently of one another are hydrogen or alkyl having 1, 2, 3 or 4 carbon atoms;

X is oxygen or NR(72);

R(72) is hydrogen or alkyl having 1, 2, 3 or 4 carbon atoms;

and their pharmaceutically tolerable salts; but where compounds are excluded in which the radicals R(1) to R(7) and also R(72) all are equal to hydrogen.

Preferred compounds of the formula I are those in which:

R(1), R(2) and R(3) independently of one another are —Y—{4—R(8)-phenyl}, —Y—{3—R(8)-phenyl} or —Y—{2—R(8)-phenyl}, where the phenyl is in each case unsubstituted or substituted by a substituent selected from the group consisting of F, Cl, —CF$_3$, methyl, methoxy and —NR(96)R(97); R(96) and R(97) independently of one another are hydrogen or —CH$_3$;

Y is a bond, oxygen, —S— or —NR(9);

R(9) is hydrogen or methyl;

R(8) is SO$_a${NR(98)}$_b$NR(99)R(10);

a is 1 or 2;

b is 0 or 1;

a+b=2;

R(98) is hydrogen, alkyl having 1, 2, 3, 4 or 5 carbon atoms or benzyl;

R(99) and R(10) independently of one another are hydrogen, alkyl having 1 or 2 carbon atoms, benzyl, —(C$_2$-C$_3$)-alkylene—NR(11)R(12), (C$_2$-C$_3$)-alkylene—NR(13)—(C$_2$-C$_3$)-alkylene—NR(37)R(38) or (C$_0$-C$_2$)-alkylene—CR(39)R(40)-CR(41)R(42)(C$_0$-C$_2$)-alkylene—(NR(43)R(44); R(11), R(12), R(13), R(37), R(38), R(43) and R(44) independently of one another are hydrogen, methyl or ethyl; R(39), R(40), R(41) and R(42) independently of one another are hydrogen, alkyl having 1, 2, 3 or 4 carbon atoms or benzyl, where the phenyl is unsubstituted or substituted by a substituent selected from the group consisting of F, Cl, —CF$_3$, methyl and methoxy;

or

R(99) and R(10) together are 4, 5 or 6 methylene groups, of which one CH$_2$ group can be replaced by oxygen, —S—, —NH— or —N—CH$_3$;

or

R(8) is SO$_a${N R(98)}$_b$NR(95)—C{=N—R(94)}—NR(93)R(92); R(95) is hydrogen; R(92), R(93) and R(94) independently of one another are hydrogen or alkyl having 1, 2, 3 or 4 carbon atoms;

or

R(1), R(2) and R(3) independently of one another are pyrrol-1-yl, pyrrol-2-yl or pyrrol-3-yl, which is unsubstituted or substituted by 1–2 substituents selected from the group consisting of F, Cl, Br, I, —CN, (C$_2$-C$_5$)-alkanoyl, (C$_2$-C$_5$)-alkoxycarbonyl, formyl, carboxyl, —CF$_3$ and methyl;

or

R(1), R(2) and R(3) independently of one another are hydrogen or alkyl having 1, 2, 3 or 4 carbon atoms;

or

R(1), R(2) and R(3) independently of one another are —Q—4—{(CH$_2$)$_k$—CH(NR(21)R(22))—(C=O)R(20)}-phenyl, —Q—3—{(CH$_2$)$_k$—CH(NR(21)R(22))—(C=O)R(20)}-phenyl or —Q—2—{(CH$_2$)$_k$—CH(NR(21)R(22))—(C=O)R(20)}-phenyl, where the phenyl in each case is unsubstituted or substituted by 1–2 substituents selected from the group consisting of F, Cl, —CF$_3$, methyl hydroxyl, methoxy, or —NR(35)R(36); R(35) and R(36) independently of one another are hydrogen or —CH$_3$;

Q is a bond, oxygen, —S— or —NR(18);

R(18) is hydrogen or —(C$_1$-C$_4$)-alkyl;

R(21) and R(22) independently of one another are hydrogen, —(C$_1$-C$_5$)-alkyl, —(C$_1$-C$_5$)-alkanoyl, —(C$_1$-C$_5$)-alkoxycarbonyl, benzyl, or benzyloxycarbonyl;

or

R(21) is trityl;

R(20) is —OR(23) or —NR(23)R(24); R(23) and R(24) independently of one another are hydrogen, —(C$_1$-C$_4$)-alkyl or benzyl;

k is zero, 1 or 2;

or

R(1), R(2) and R(3) independently of one another are (C$_1$-C$_9$)-heteroaryl, which is linked via C or N and which is unsubstituted or substituted by a substituent selected from the group consisting of F, Cl, CF$_3$, CH$_3$, methoxy and dimethylamino;

or

R(1), R(2) and R(3) are —SR(25), —OR(25), —NR(25)R(26), —CR(25)R(26)R(27);

R(25) is —C$_f$H$_{2f}$—(C$_1$-C$_9$)-heteroaryl, which is unsubstituted or substituted by a substituent selected from the group consisting of F, Cl, CF$_3$, CH$_3$, methoxy, dimethylamino;

f is zero, 1 or 2;

R(26) and R(27) independently of one another are defined as R(25) or are hydrogen or methyl;

or

R(1), R(2) and R(3) independently of one another are (C$_1$-C$_9$)-heteroaryl N-oxide, which is linked via C or N and which is unsubstituted or substituted by 1–2 substituents selected from the group consisting of F, Cl, CF$_3$, CH$_3$, methoxy, hydroxyl, amino, methylamino and dimethylamino;

or

R(1), R(2) and R(3) independently of one another are —SR(28), —OR(28), —NR(28)R(29) or —CR(28)R(29)R(30);

R(28) is —C$_g$H$_{2g}$—(C$_1$-C$_9$)-heteroaryl N-oxide, which is unsubstituted or substituted by 1–2 substituents selected from the group consisting of F, Cl, CF$_3$, CH$_3$, methoxy, hydroxyl, amino, methylamino and dimethylamino;

g is zero or 1, R(29) and R(30) independently of one another are defined as R(28) or are hydrogen or methyl;

or

R(1), R(2) and R(3) independently of one another are hydrogen, F, Cl, CF$_3$, R(31)SO$_2$—, R(32)R(33)N—CO—, R(34)—CO— or R(45)R(46)N—SO$_2$; R(31) and R(34) independently of one another are methyl or —CF$_3$; R(32), R(33), R(45) and R(46) independently of one another are hydrogen or methyl;

or

R(1), R(2) and R(3) independently of one another are R(51)—A—G—D—; R(51) is —NR(52)R(53), an amidino group R(52)R(53)N—C{=N—R(54)}— or a guanidino group R(52)R(53)N—C{=N—R(54)}—NR(55)—; R(52), R(53), R(54) and R(55) independently of one another are hydrogen or alkyl having 1, 2, 3 or 4 carbon atoms;

or

R(52) and R(53) are a group C$_\alpha$H$_{2\alpha}$;

α is 4, 5, 6 or 7;

where if α=5, 6 or 7 a carbon atom of the group C$_\alpha$H$_{2\alpha}$ can be replaced by a heteroatom group O, SO$_d$ or NR(56);

or

R(53) and R(54) are a group C$_\gamma$H$_{2\gamma}$,

γ is 2, 3, 4 or 5;

where if γ=3, 4 or 5 a carbon atom of the group C$_\gamma$H$_{2\gamma}$ can be replaced by a heteroatom group O, SO$_d$ or NR(56);

d is zero or 2;

R(56) is hydrogen or methyl;

or
R(51) is imidazolyl, pyridyl, quinolinyl or isoquinolinyl;
A is a group $C_eH_{2e}$;
e is zero, 1, 2, 3, 4 or 5;
where in the group $C_eH_{2e}$ a carbon atom can be replaced by one of the groups —O—, —CO—, —CH{OR(57)}—, —SO$_r$—, —NR(57)—, —NR(57)—CO—, —NR(57)—CO—NH—, —NR(57)—CO—NH—SO$_2$— or —NR(57)—SO$_2$—;
r is zero or 2;
G is a phenylene radical

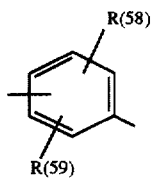

R(58) and R(59) independently of one another are hydrogen, methyl, F, Cl, CF$_3$ or —SO$_2$—R(60); R(60) is methyl or NR(61)R(62); R(61) and R(62) independently of one another are hydrogen or methyl;
D is —C$_v$H$_{2v}$—E$_w$—;
v is zero, 1, 2, 3 or 4;
E is —O—, —CO—, —CH{OR(63)}—, —SO$_{aa}$— or —NR(63)—;
w is zero or 1;
aa is zero or 2
R(63) is hydrogen or methyl;

or
R(2) is —CF$_2$R(64), —CF{R(65)}{R(66)}, —CF(CF$_3$){R(65)}, —C(CF$_3$)=CR(65)R(66); R(64) is alkyl having 1, 2, 3 or 4 carbon atoms or cycloalkyl having 3, 4, 5, 6 or 7 carbon atoms; R(65) and R(66) independently of one another are hydrogen or alkyl having 1, 2, 3 or 4 carbon atoms;

or
R(1), R(2) and R(3) independently of one another are —OR(67) or —NR(67)R(68); R(67) and R(68) independently of one another are hydrogen or alkyl having 1,2 or 3 carbon atoms;

or
R(67) and R(68) together are 4, 5 or 6 methylene groups, of which one CH$_2$ group can be replaced by oxygen, —S—, SO$_2$, —NH— or —NCH$_3$;
R(4) and R(5) independently of one another are hydrogen, alkyl having 1, 2 or 3 carbon atoms, F, Cl, —OR(69), —NR(70)R(71) or —CF$_3$; R(69), R(70) and R(71) independently of one another are hydrogen or methyl;
R(6) and R(7) independently of one another are hydrogen or methyl;
X is oxygen or NR(72)
R(72) is hydrogen or methyl;
and their pharmaceutically tolerable salts.
Particularly preferred compounds of the formula I are those in which:
R(1), R(2) and R(3) independently of one another are —O—{4—R(8)-phenyl}, the phenyl in each case is unsubstituted or substituted by a substituent selected from the group consisting of F, Cl, —CF$_3$, methyl and methoxy;
R(8) is SO$_a${NR(98)}$_b$NR(99)R(10);
a is 1 or 2;
b is 0 or 1;
a+b=2;
R(98) is hydrogen or alkyl having 1, 2, 3 or 4 carbon atoms;
R(99) and R(10) independently of one another are hydrogen, alkyl having 1 or 2 carbon atoms, benzyl, —(C$_2$-C$_3$)-alkylene—NR(11)R(12), (C$_2$-C$_3$)-alkylene—NR(13)—(C$_2$-C$_3$)-alkylene—NR(37)R(38) or (C$_0$-C$_2$)-alkylene—CR(39)R(40)—CR(41)R(42) (C$_0$-C$_2$)-alkylene—NR(43)R(44); R(11), R(12), R(13), R(37), R(38), R(43) and R(44) independently of one another are hydrogen, methyl or ethyl; R(39), R(40), R(41) and R(42) independently of one another are hydrogen, alkyl having 1, 2, 3 or 4 carbon atoms or benzyl, where the phenyl is unsubstituted or substituted by a substituent selected from the group consisting of F, Cl, —CF$_3$, methyl and methoxy;

or
R(99) and R(10) together are 4, 5 or 6 methylene groups, of which one CH$_2$ group can be replaced by —NH— or —N—CH$_3$;

or
R(8) is SO$_a${NR(98)}$_b$NR(95)—C{=N—R(94)}—NR(93)R(92); R(95) is hydrogen; R(92), R(93) and R(94) independently of one another are hydrogen or alkyl having 1, 2, 3 or 4 carbon atoms;

or
R(1), R(2) and R(3) independently of one another are pyrrol-1-yl, which is unsubstituted or substituted by 1-2 substituents selected from the group consisting of F, Cl, Br, I, —CN, acetyl, (C$_2$-C$_5$)-alkoxycarbonyl, —CF$_3$ and methyl;

or
R(1), R(2) and R(3) independently of one another are hydrogen or alkyl having 1, 2, 3 or 4 carbon atoms;

or
R(1), R(2) and R(3) independently of one another are —Q—4—{(CH$_2$)$_k$—CH(NR(21)R(22))—(C=O)R(20)}-phenyl, where the phenyl in each case is unsubstituted or substituted by a substituent from the group consisting of F, Cl, —CF$_3$, methyl, hydroxyl and methoxy;
Q is a bond or oxygen;
R(21), R(22) independently of one another are hydrogen, methyl, —(C$_1$-C$_5$)-alkanoyl, —(C$_1$-C$_5$)-alkoxycarbonyl, benzyl or benzyloxycarbonyl;
R(20) is —OR(23) or —NR(23)R(24); R(23), R(24) independently of one another are hydrogen, —(C$_1$-C$_4$)-alkyl or benzyl;
k is zero, 1 or 2;

or
R(1), R(2) and R(3) independently of one another are imidazolyl, which is linked via C or N and which is unsubstituted or substituted by a substituent selected from the group consisting of F, Cl, CF$_3$, CH$_3$ and methoxy;

or
R(1), R(2) and R(3) are —SR(25), —OR(25), —NR(25)R(26), —CR(25)R(26)R(27); R(25) is —(C$_1$-C$_9$)-heteroaryl, which is unsubstituted or substituted by a substituent selected from the group consisting of F, Cl, CF$_3$, CH$_3$ and methoxy; R(26), R(27) independently of one another are hydrogen or methyl;

or
R(1), R(2) and R(3) independently of one another are —SR(28), —OR(28), —NR(28)R(29) or —CR(28)R (29)R(30); R(28) is —(C$_1$–C$_9$)-heteroaryl N-oxide, which is unsubstituted or substituted by a substituent selected from the group consisting of F, Cl, CF$_3$, CH$_3$ and methoxy; R(29) and R(30) independently of one another are hydrogen or methyl;

or

R(1), R(2) and R(3) independently of one another are hydrogen, F, Cl, CF$_3$, R(31)SO$_2$—, R(32)R(33)N—CO—, R(34)—CO— or R(45)R(46)N—SO$_2$; R(31) and R(34) independently of one another are methyl or —CF$_3$; R(32), R(33), R(45) and R(46) independently of one another are hydrogen or methyl;

or

R(2) is R(51)—A—G—D—; R(51) is —NR(52)R(53), an amidino group R(52)R(53)N—C{=N—R(54)}— or a guanidino group R(52)R(53)N—C{=N—R(54)}—NR(55)—; R(52), R(53), R(54) and R(55) independently of one another are hydrogen or alkyl having 1, 2, 3 or 4 carbon atoms;

or

R(52) and R(53) are a group C$_\alpha$H$_{2\alpha}$;
α is 4, 5, 6 or 7;
where if α=5, 6 or 7 a carbon atom of the group C$_\alpha$H$_{2\alpha}$ can be replaced by a heteroatom group O, SO$_d$ or NR(56), or R(53) and R(54) are a group C$_\gamma$H$_{2\gamma}$;
γ is 2, 3, 4 or 5;
where if γ=3, 4 or 5 a carbon atom of the group C$_\gamma$H$_{2\gamma}$ can be replaced by a heteroatom group O, SO$_d$ or NR(56);
d is zero or 2;
R(56) is hydrogen or methyl;

or

R(51) is imidazolyl, pyridyl, quinolinyl or isoquinolinyl;
A is C$_e$H$_{2e}$;
e is zero, 1, 2, 3, 4 or 5;
where in the group C$_e$H$_{2e}$ a carbon atom can be replaced by one of the groups —O—, —CO—, —CH{OR(57)}—, —SO$_r$—, —NR(57)—, —NR(57)—CO—, —NR(57)—CO—NH—, —NR(57)—CO—NH—SO$_2$— or —NR(57)—SO$_2$—;
r is zero or 2;
G is a phenylene radical

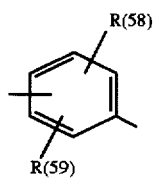

R(58) and R(59) independently of one another are hydrogen, methyl, F, Cl, CF$_3$ or —SO$_2$—R(60); R(60) is methyl or NR(61)R(62); R(61) and R(62) independently of one another are hydrogen or methyl;
D is —C$_v$H$_{2v}$—E$_w$—,
v is zero, 1, 2, 3 or 4;
E is —O—, —CO—, —CH{OR(63)}—, —SO$_{aa}$— or —NR(63)—;
w is zero or 1;
aa is zero or 2
R(63) is hydrogen or methyl;

or

R(2) is —CF$_2$R(64), —CF{R(65)}{R(66)}, —CF(CF$_3$){R(65)}, —C(CF$_3$)=CR(65)R(66); R(64) is alkyl having 1, 2, 3 or 4 carbon atoms or cycloalkyl having 3, 4, 5, 6 or 7 carbon atoms; R(65) and R(66) independently of one another are hydrogen or alkyl having 1, 2, 3 or 4 carbon atoms;

or

R(1), R(2) and R(3) independently of one another are —OR(67) or —NR(67)R(68); R(67) and R(68) independently of one another are hydrogen or alkyl having 1, 2 or 3 carbon atoms;

or

R(67) and R(68) together are 4, 5 or 6 methylene groups, of which one CH$_2$ group can be replaced by oxygen, —S—, SO$_2$, —NH— or —NCH$_3$;

R(4) and R(5) independently of one another are hydrogen, alkyl having 1, 2 or 3 carbon atoms, F, Cl, —OR(69), —NR(70)R(71) or —CF$_3$; R(69), R(70) and R(71) independently of one another are hydrogen or methyl;

R(6) and R(7) independently of one another are hydrogen or methyl;

X is oxygen or NR(72) R(72) is hydrogen or methyl;
and their pharmaceutically tolerable salts.

Very particularly preferred compounds of the formula I are those in which:

R(2) is —O—{4—R(8)-phenyl}, where the phenyl in each case is unsubstituted or substituted by a substituent selected from the group consisting of F, Cl, —CF$_3$, methyl and methoxy;

R(8) is SO$_a$\{NR(98)\}$_b$NR(99)R(10);
a is 1 or 2;
b is 0 or 1;
a+b=2;
R(98) is hydrogen or alkyl having 1, 2, 3 or 4 carbon atoms;

R(99) and R(10) independently of one another are hydrogen, alkyl having 1 or 2 carbon atoms, —(C$_2$–C$_3$)-alkylene—NR(11)R(12), (C$_2$–C$_3$)-alkylene—NR(13)—(C$_2$–C$_3$)-alkylene—NR(37)R(38) or (C$_0$–C$_2$)-alkylene—CR(39)R(40)—CR(41)R(42)(C$_0$–C$_2$)-alkylene—NR(43)R(44); R(11), R(12), R(13), R(37), R(38), R(43) and R(44) independently of one another are hydrogen, methyl or ethyl; R(39), R(40), R(41) and R(42) independently of one another are hydrogen, alkyl having 1, 2, 3 or 4 carbon atoms or benzyl, where the phenyl is unsubstituted or substituted by a substituent selected from the group consisting of methyl and methoxy;

or

R(99) and R(10) together are 5 or 6 methylene groups, of which one CH$_2$ group can be replaced by —NH— or —N—CH$_3$;

or

R(8) is SO$_a$\{NR(98)\}$_b$NR(95)—C{=N—R(94)}—NR(93)R(92);
R(95) is hydrogen; R(92), R(93) and R(94) independently of one another are hydrogen or alkyl having 1, 2, 3 or 4 carbon atoms;

or

R(1) is pyrrol-1-yl, which is unsubstituted or substituted by 1–2 substituents selected from the group consisting of F, Cl, Br, I, —CN, acetyl, —CF$_3$ and methyl;

or

R(1), R(2) and R(3) independently of one another are hydrogen or alkyl having 1, 2, 3 or 4 carbon atoms;

or

R(2) is —O—4—{CH$_2$—CH(NR(21)R(22))—(C=O)R(20)}-phenyl, where the phenyl is unsubstituted or substituted by a substituent selected from the group consisting of F, Cl, —CF$_3$, methyl, hydroxyl and methoxy; R(21), R(22) independently of one another are hydrogen, methyl, —(C$_1$–C$_5$)-alkanoyl, —(C$_1$–C$_5$)-alkoxycarbonyl, benzyl or benzyloxycarbonyl; R(20) is —OR(23) or —NR(23)R(24); R(23) and R(24) independently of one another are hydrogen or —(C$_1$–C$_4$)-alkyl;

or

R(2) is imidazolyl, which is linked via C or N and which is unsubstituted or substituted by a substituent selected from the group consisting of F, Cl, CF$_3$, CH$_3$ and methoxy;

or

R(2) is —SR(25) or —OR(25); R(25) is pyridyl, quinolinyl or isoquinolinyl, which in each case are unsubstituted or substituted by a substituent selected from the group consisting of F, Cl, CF$_3$, CH$_3$ and methoxy;

or

R(2) is —SR(28) or —OR(28); R(28) is pyridyl N-oxide, quinolinyl N-oxide or isoquinolinyl N-oxide, which in each case are unsubstituted or substituted by a substituent selected from the group consisting of F, Cl, CF$_3$, CH$_3$ and methoxy;

or

R(1) is hydrogen, F, Cl, CF$_3$, R(31)SO$_2$—, R(32)R(33)N—CO—, R(34)—CO— or R(45)R(46)N—SO$_2$; R(31) and R(34) independently of one another are methyl or —CF$_3$; R(32), R(33), R(45) and R(46) independently of one another are hydrogen or methyl;

or

R(2) is R(51)—A—G—O—; R(51) is —NR(52)R(53), an amidino group R(52)R(53)N—C{=N—R(54)}— or a guanidino group R(52)R(53)N—C{=N—R(54)}—NR(55)—; R(52), R(53), R(54) and R(55) independently of one another are hydrogen or alkyl having 1 or 2 carbon atoms;

or

R(52) and R(53) are a group C$_\alpha$H$_{2\alpha}$;
α is 5 or 6;
where a carbon atom of the group C$_\alpha$H$_{2\alpha}$ can be replaced by NR(56);
R(56) is hydrogen or methyl;

or

R(51) is imidazolyl, pyridyl, quinolinyl or isoquinolinyl;
A is C$_e$H$_{2e}$;
e is zero, 1, 2 or 3;
where in the group C$_e$H$_{2e}$ a carbon atom can be replaced by one of the groups —O—, —CO—, —CH{OR(57)}—, —SO$_r$—, —NR(57)—, —NR(57)—CO—, —NR(57)—CO—NH—, —NR(57)—CO—NH—SO$_2$— or —NR(57)—SO$_2$—;
r is zero or 2;
G is a phenylene radical

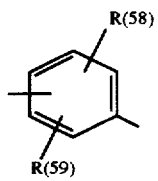

R(58) and R(59) independently of one another are hydrogen, methyl, F, Cl, CF$_3$ or —SO$_2$—R(60); R(60) is methyl or NR(61)R(62); R(61) and R(62) independently of one another are hydrogen or methyl;

or

R(2) is —CF$_2$R(64), —CF{R(65)}{R(66)}, —CF(CF$_3$){R(65)}, —C(CF$_3$)=CR(65)R(66);

R(64) is alkyl having 1, 2, 3 or 4 carbon atoms or cycloalkyl having 5 or 6 carbon atoms;

R(65) and R(66) independently of one another are hydrogen or alkyl having 1, 2, 3 or 4 carbon atoms;

or

R(1), R(2) and R(3) independently of one another are —OR(67) or —NR(67)R(68); R(67) and R(68) independently of one another are hydrogen, methyl or ethyl;

or

R(67) and R(68) together are 4 or 5 methylene groups, of which one CH$_2$ group can be replaced by oxygen, —NH— or —NCH$_3$.

R(4) and R(5) independently of one another are hydrogen, alkyl having 1, 2 or 3 carbon atoms, F, Cl, or —CF$_3$;

R(6) and R(7) independently of one another are hydrogen or methyl;

X is oxygen or NR(72) R(72) is hydrogen or methyl;

and their pharmaceutically tolerable salts.

Especially preferred compounds of the formula I are those in which:

R(2) is —O—{4—R(8)-phenyl},
R(8) is SO$_a${NR(98)}$_b$NR(99)R(10);
a is 1 or 2;
b is 0 or 1;
a+b=2;
R(98) is hydrogen or alkyl having 1, 2, 3 or 4 carbon atoms;
R(99) and R(10) independently of one another are hydrogen, alkyl having 1 or 2 carbon atoms, —(C$_2$–C$_3$)-alkylene—NR(11)R(12); R(11) and R(12) independently of one another are hydrogen, methyl or ethyl;

or

R(99) and R(10) together are 5–6 methylene groups, of which one CH$_2$ group can be replaced by —NH— or —N—CH$_3$;

or

R(8) is SO$_a${NR(98)}$_b$NR(95)—C{=N—R(94)}—NR(93)R(92);
R(95) is hydrogen;
R(92), R(93) and R(94) independently of one another are hydrogen or alkyl having 1, 2, 3 or 4 carbon atoms;

or

R(1) is pyrrol-1-yl, which is unsubstituted or substituted by 1-2 substituents selected from the group consisting of F, Cl, Br, I, —CN, acetyl, —CF$_3$ and methyl;

or

R(1), R(2) and R(3) independently of one another are hydrogen or alkyl having 1, 2, 3 or 4 carbon atoms;

or

R(2) is —O—4—{CH$_2$—CH(NR(21)R(22))—(C=O)R(20)}-phenyl,
R(21) and R(22) independently of one another are hydrogen, methyl, —(C$_1$–C$_5$)-alkanoyl, —(C$_1$–C$_5$)-alkoxycarbonyl, benzyl, or benzyloxycarbonyl;
R(20) is —OR(23) or —NR(23)R(24); R(23) and R(24) independently of one another are hydrogen or —(C$_1$–C$_4$)-alkyl;

or

R(2) is imidazolyl which is linked via C or N;

or

R(2) is —SR(25) or —OR(25);

R(25) is pyridyl, quinolinyl or isoquinolinyl, which is unsubstituted or substituted by a substituent selected from the group consisting of F, Cl, CF$_3$, CH$_3$ and methoxy;

or

R(2) is —SR(28) or —OR(28);

R(28) is pyridyl N-oxide, quinolinyl N-oxide or isoquinolinyl N-oxide, which is unsubstituted or substituted by a substituent selected from the group consisting of F, Cl, CF$_3$, CH$_3$ and methoxy;

or

R(1) is hydrogen, F, Cl, CF$_3$, R(31)SO$_2$— or R(45)R(46)N—SO$_2$;

R(31) is methyl or —CF$_3$; R(45) and R(46) independently of one another are hydrogen or methyl;

or

R(2) is R(51)—A—G—O;

R(51) is —NR(52)R(53); R(52) and R(53) independently of one another are hydrogen or alkyl having 1 or 2 carbon atoms;

or

R(52) and R(53) are C$_\alpha$H$_{2\alpha}$;

α is 5 or 6;

where a carbon atom of the group C$_\alpha$H$_{2\alpha}$ can be replaced by NR(56), R(56) is hydrogen or methyl;

or

R(51) is imidazolyl, pyridyl, quinolinyl or isoquinolinyl

A is C$_e$H$_{2e}$;

e is zero, 1, 2 or 3;

where in the group C$_e$H$_{2e}$ a carbon atom can be replaced by one of the groups —O—, —CH{OR(57)}—, SO$_r$—, —NR(57)—, or —NR(57)—SO$_2$—;

r is zero or 2;

G is a phenylene radical

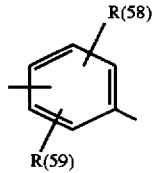

or

R(2) is —CF$_2$R(64), —CF{R(65)}{R(66)}, —CF(CF$_3$){R(65)}, —C(CF$_3$)=CR(65)R(66);

R(64) is alkyl having 1, 2, 3 or 4 carbon atoms or cycloalkyl having 5 or 6 carbon atoms;

R(65) and R(66) independently of one another are hydrogen or alkyl having 1, 2, 3 or 4 carbon atoms;

or

R(1), R(2) and R(3) independently of one another are —OR(67) or —NR(67)R(68); R(67) and R(68) independently of one another are hydrogen, methyl or ethyl;

or

R(67) and R(68) together are 4–5 methylene groups, of which one CH$_2$ group can be replaced by oxygen, —NH— or —NCH$_3$;

R(4) and R(5) independently of one another are hydrogen, alkyl having 1, 2 or 3 carbon atoms, F, Cl or —CF$_3$;

R(6) and R(7) independently of one another are hydrogen or methyl;

X is oxygen or NR(72);

R(72) is hydrogen or methyl;

and their pharmaceutically tolerable salts.

If one of the compounds of the formula I contains one or more centers of asymmetry, these centers independently of one another can have either the S-configuration or the R-configuration. The compounds can be present as optical isomers, as diastereomers, as racemates or as mixtures thereof.

The alkyl and perfluoroalkyl radicals indicated can be either straight-chain or branched.

(C$_1$–C$_9$)-Heteroaryl is understood to mean radicals which are derived from phenyl or naphthyl, in which one or more CH groups are replaced by N and/or in which at least two neighboring CH groups (with the formation of a five-membered aromatic ring) are replaced by S, NH or O. In addition, one or both the atoms of the fusion site of bicyclic radicals (as in indolizinyl) can also be N atoms.

Heteroaryl, in particular, is furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl.

The invention furthermore relates to a process for preparing a compound of the formula I, which comprises reducing a compound of the formula II

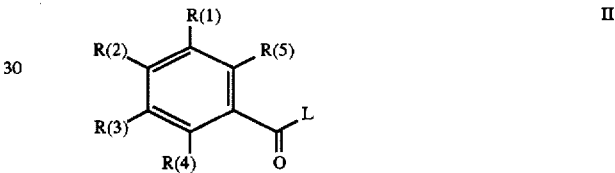

in which R(1) to R(5) have the meanings given above, or reacting it with a carbon nucleophile. Intermediates of the formula III

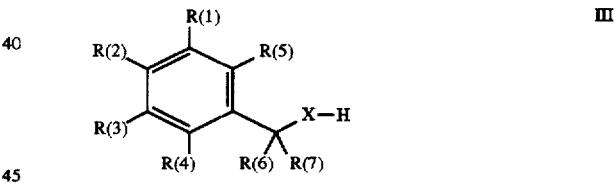

are obtained, where R(1) to R(7) and X have the meaning given above.

The acid derivatives of the formula II, in which L is an amino, alkylamino or guanidino group, or an alkoxy, preferably a methoxy, group, a phenoxy group, phenylthio, methylthio or 2-pyridylthio group, or a nitrogen heterocycle, preferably 1-imidazolyl, are advantageously obtained, in a manner known per se, from the underlying carbonyl chlorides (formula II, L=Cl), which, for their part, can in turn be prepared, in a manner known per se, from the underlying carboxylic acids (formula II, L=OH), for example using thionyl chloride.

In addition to the carbonyl chlorides of the formula II (L=Cl), further acid derivatives of the formula II can also be prepared, in a manner known per se, directly from the underlying benzoic acid derivatives (formula II, L=OH), such as, for example, the methyl esters of the formula II with L=OCH$_3$ by treating with gaseous HCl in methanol, the imidazolides of the formula II by treating with carbonyldiimidazole {L=1-imidazolyl, Staab, Angew. Chem. Int. Ed. Engl. 1, 351–367 (1962)}, the mixed anhydrides II with Cl—COOC$_2$H$_5$ or tosyl chloride in the presence of triethylamine in an inert solvent, as well as the activation of benzoic acids with dicyclohexylcarbodiimide (DCC) or with O-{(cyano(ethoxycarbonyl)methylene)amino}-1,1,3,3-tetramethyluronium tetrafluoroborate ("TOTU") {Proceedings of the 21st European Peptide Symposium, Peptides 1990, Editors E. Giralt and D. Andreu, Escom, Leiden, 1991}. A series of suitable methods for preparing activated carboxylic acid derivatives of the formula II are given, with citation of the source literature, in J. March, Advanced Organic Chemistry, Third Edition (John Wiley & Sons, 1985), p. 350.

Reaction of the intermediates of the formula III to give the acylguanidines of the formula I is carried out by means of reaction with a suitable carbonic acid derivative, preferably phosgene, diphosgene (trichloromethyl chloroformate), triphosgene (bis(trichloromethyl carbonate)), ethyl chloroformate, i-butyl chloroformate, bis(1-hydroxy-1H-benzotriazolyl) carbonate and N,N'-carbonyldiimidazole, in a solvent which is inert to the reagents used, preferably DMF, THF or toluene, at a temperature between −20° C. and the boiling point of the solvent, preferably between 0° C. and 60° C., first to give a substituted carbonic acid derivative of the formula IV

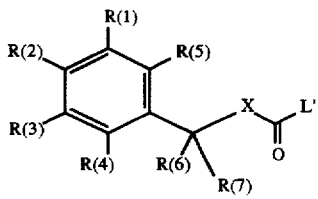

IV in which R(1) to R(7) and X have the meaning given above and L', depending on the carbonic acid derivative used, is chlorine, ethoxy, isobutoxy, benzotriazol-1-oxy or 1-imidazolyl. The guanylation of the carbonic acid derivatives of the formula IV to give the compounds of the formula I according to the invention is preferably carried out in the same solvent at a temperature between 0° C. and 60° C. without prior purification having taken place.

The unknown compounds of the formula II can be prepared by methods known from the literature by converting, for example, 4-halo-3-chlorosulfonylbenzoic acids into 3-aminosulfonyl-4-halobenzoic acids using ammonia or amines or into 3-alkylsulfonyl-4-halobenzoic acids using a weak reductant such as sodium bisulfite and subsequent alkylation, and reacting according to one of the process variants described above to give compounds I according to the invention.

The introduction of the benzenesulfonamide derivatives substituted in the phenyl moiety by sulfur, oxygen or nitrogen nucleophiles is carried out by methods of nucleophilic aromatic substitution known from the literature. Leaving groups on the benzoic acid derivative which have proven suitable in this substitution are halides and trifluoromethanesulfonates. The reaction is advantageously carried out in a dipolar aprotic solvent, such as DMF or TMU, at a temperature from 0° C. up to the boiling point of the solvent, preferably from 80° C. up to the boiling point of the solvent. The acid scavenger advantageously used is an alkali metal or alkaline earth metal salt with an anion of high basicity and low nucleophilicity, for example $K_2CO_3$ or $CsCO_3$.

The introduction of the alkyl or aryl substituents is carried out by methods known from the literature of palladium-mediated cross-coupling of aryl halides with, for example, organozinc compounds, organostannanes, organoboronic acids or organoboranes.

Acylguanidines I are in general weak bases and are able to bind acid with the formation of salts. Suitable acid addition salts are salts of all pharmacologically tolerated acids, for example halides, in particular hydrochlorides, ascorbates, lactates, sulfates, citrates, tartrates, acetates, phosphates, methanesulfonates and p-toluenesulfonates.

Only benzoylguanidines are described in U.S. Pat. No. 5,091,394. Alkanoylguanidines, however, are not mentioned anywhere, nor is inhibition of the cellular $Na^+/H^+$ exchange mechanism by them.

It was therefore surprising that the compounds of the formula I are potent inhibitors of this system.

Compared with the prior art, the compounds of the formula I are distinguished by an increased stability to solvolysis.

As a consequence of their pharmacological properties, the compounds I are outstandingly suitable as antiarrhythmic pharmaceuticals having a cardioprotective component for the prophylaxis and treatment of infarction as well as for the treatment of angina pectoris, the compounds also inhibiting or strongly reducing, in a preventive manner, the pathophysiological processes in association with the occurrence of ischemically induced damage, in particular in association with the elicitation of ischemically induced cardiac arrhythmias. On account of their protective effects against pathological hypoxic and ischemic situations, the compounds of the formula I according to the invention can be used, as a consequence of inhibition of the cellular $Na^+/H^+$ exchange mechanism, as pharmaceuticals for treating all acute or chronic damage elicited by ischemia, or illnesses which are primarily or secondarily induced thereby. This applies to their use as pharmaceuticals for surgical interventions, e.g. in association with organ transplants, it being possible to use the compounds to protect the organs in the donor before and during removal and to protect removed organs, for example when being treated with physiological bathing fluids or when being stored in these fluids, and also in association with transfer of the organs into the recipient subject. The compounds are likewise valuable protective pharmaceuticals for use when carrying out angioplastic surgical interventions, for example on the heart or on peripheral vessels. In accordance with their protective action against ischemically induced damage, the compounds are also suitable for use as pharmaceuticals for treating ischemias of the nervous system, in particular of the CNS, where they are suitable e.g. for the treatment of stroke or of cerebral edema. In addition to this, the compounds of the formula I according to the invention are likewise suitable for use in the treatment of forms of shock, such as, for example, allergic, cardiogenic, hypovolemic and bacterial shock.

In addition to this, the compounds of the formula I according to the invention are notable for their strong inhibitory effect on the proliferation of cells, for example the proliferation of fibroblast cells and the proliferation of the smooth muscle cells of the vasculature. For this reason, the compounds of the formula I are suitable, as valuable therapeutic agents, for use in diseases in which cell proliferation represents a primary or secondary cause, and may therefore be used as antiatherosclerotic agents, and as agents against diabetic late complications, carcinomatous disorders, fibrotic disorders such as pulmonary fibrosis, hepatic fibrosis or renal fibrosis, and against organ hypertrophy and hyperplasia, in particular in hyperplasia or hypertrophy of the prostate.

The compounds according to the invention are efficacious inhibitors of the cellular sodium/proton antiporter ($Na^+/H^+$ exchanger), which, in numerous disorders (essential hypertension, atherosclerosis, diabetes, etc.), is also elevated in those cells which are readily accessible to measurement, such as, for example, in erythrocytes, blood platelets or leukocytes. The compounds according to the invention are therefore suitable for use as outstanding, simple, scientific tools, for example in their use as diagnostics for determining and differentiating particular forms of hypertension, but also for use in atherosclerosis, diabetes, proliferative disorders, and so on. In addition, the compounds of the formula I are suitable for use in preventive therapy for preventing the genesis of high blood pressure, for example of essential hypertension.

In this context, pharmaceuticals which contain a compound I can be administered orally, parenterally, intravenously or rectally, or by inhalation, the preferred route of administration being dependent on how the disorder manifests itself. In this context, the compounds I may be used alone or together with pharmaceutical auxiliary substances to form a pharmaceutical composition, both in the case of veterinary medicine and in the case of human medicine.

Owing to his specialist knowledge, the person skilled in the art is familiar with which auxiliary substances are suitable for the desired pharmaceutical formulation. In addition to solvents, gel formers, suppository bases, tablet auxiliary substances, and other active-compound excipients, antioxidants, dispersing agents, emulsifiers, defoamers, taste corrigents, preservatives, solubilizers or dyes, for example, can be used.

In order to prepare a form for oral use, the active compounds are mixed with the additives which are suitable for the purpose, such as excipient substances, stabilizers or inert diluents, and converted by the customary methods into the forms suitable for administration, such as tablets, coated tablets, hard gelatin capsules or aqueous, alcoholic or oily solutions. Gum arabic, magnesia, magnesium carbonate, potassium phosphate, lactose, glucose or starch, in particular corn starch, for example, can be used as inert excipients. In this context, the preparation can be effected as dry or wet granules. Vegetable or animal oils, for example, such as sunflower oil or cod-liver oil, are suitable for use as oily carrier substances or as solvents.

For subcutaneous or intravenous administration, the active compounds, if desired together with the substances which are customary for the purpose, such as solubilizers, emulsifiers or additional auxiliary substances, are brought into solution, suspension or emulsion. Examples of suitable solvents are: water, physiological saline solution, or alcohols, for example ethanol, propanol or glycerol, and in addition sugar solutions, such as glucose or mannitol solutions, or alternatively a mixture of the different solvents mentioned.

Solutions, suspensions or emulsions of the active compound of the formula I in a pharmaceutically harmless solvent, such as, in particular, ethanol or water, or a mixture of such solvents, are suitable for use as a pharmaceutical formulation for administration in the form of aerosols or sprays, for example. Depending on requirements, the formulation can also contain yet other pharmaceutical auxiliary substances, such as surface active agents, emulsifiers and stabilizers, as well as a propellant. Such a preparation customarily contains the active compound in a concentration of about 0.1 to 10, in particular of about 0.3 to 3% by weight.

The dosage of the active compound of the formula I to be administered, and the frequency of the administration, depend on the strength and the duration of action of the compounds used; additionally also on the nature and severity of the disease to be treated, as well as on the sex, age, weight and individual responsiveness of the mammal to be treated.

On average, the daily dose of a compound of the formula I for a patient of about 75 kg in weight is at least 0.001 mg/kg, preferably at least 0.01 mg/kg, up to at most 10 mg/kg, preferably up to at most 1 mg/kg, of body weight. In acute episodes of the disorder, for example immediately after suffering a cardiac infarct, even higher, and in particular more frequent, dosages may also be necessary, for example up to 4 individual doses per day. In association with i.v. use, in particular, for example in the case of an infarct patient in intensive care, up to 100 mg per day may be necessary.

List of abbreviations:

| | |
|---|---|
| MeOH | Methanol |
| DMF | N,N-Dimethylformamide |
| TMU | N,N,N',N'-Tetramethylurea |
| NBS | N-Bromosuccinimide |
| AIBN | α,α-Azobisisobutyronitrile |
| EI | electron impact |
| DCI | Desorption-chemical ionization |
| RT | Room temperature |
| EA | Ethyl acetate (EtOAc) |
| DIP | Diisopropyl ether |
| MTB | Methyl tertiary-butyl ether |
| mp | Melting point |
| HEP | n-Heptane |
| DME | Dimethoxyethane |
| FAB | Fast Atom Bombardment |
| CH$_2$Cl$_2$ | Dichloromethane |
| THF | Tetrahydrofuran |
| eq | Equivalent |
| ES | Electrospray ionization |
| Me | Methyl |
| Et | Ethyl |
| Bn | Benzyl |
| CNS | Central nervous system |
| Brine | Saturated aqueous NaCl solution |
| CDI | N,N'-Carbonyldiimidazole |

EXAMPLE 1

4-(3-Pyridyloxy)-3-trifluoromethyl-benzyloxycarbonylguanidine, dihydrochloride

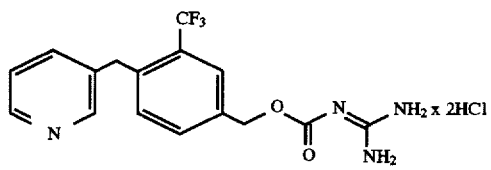

a) Methyl 4-(3-pyridyloxy)-3-trifluoromethylbenzoate 2 mmol of methyl 4-fluoro-3-trifluoromethylbenzoate, 2 mmol of 3-hydroxypyridine and 4 mmol of K$_2$CO$_3$ were stirred at 110° C. for 1.5 h in 15 ml of DMF (anhydrous). The mixture was then poured onto 100 ml of water and extracted 3 times using 50 ml of EA each time. It was dried over Na$_2$SO$_4$, the solvent was removed in vacuo and the product was reacted further without further purification.

500 mg of colorless oil.

| | |
|---|---|
| R$_f$(MTB) = 0.33 | MS (ES): 298 (M + 1)$^+$ | b) 4-(3-Pyridyloxy)-3-trifluoromethylbenzyl alcohol 0.9 g of methyl 4-(3-pyridyloxy)-3-trifluoromethylbenzoate was dissolved in 10 ml of THF and 235 mg of LiAlH$_4$ were added at 0° C. The mixture was stirred at RT for 3 h, poured onto 50 ml of 1N Na$_2$CO$_3$ and extracted 3 times with 50 ml of EA. It was dried over Na$_2$SO$_4$ and the solvent was removed in vacuo. 780 mg of a white solid were obtained, which was used without further purification.

M.p. 96° C.

| $R_f$(MTB) = 0.22 | MS (EI): 269 (M + 1)⁺ | c) 4-(3-Pyridyloxy)-3-trifluoromethylbenzyloxycarbonylguanidine, dihydrochloride 600 mg of 4-(3-pyridyloxy)-3-trifluoromethylbenzyl alcohol and 360 mg of CDI were dissolved in 10 ml of DMF and the mixture was stirred at RT for 24 h. 660 mg of guanidine were then added, and the mixture was stirred at RT for a further 24 h. The reaction mixture was poured onto 100 ml of water and stirred at RT for one hour, and the product was filtered S off. It was then taken up in 50 ml of 0.1N aqueous HCl solution, and water and excess HCl were removed in vacuo.

750 mg of the dihydrochloride are obtained, m.p. 130° C. (decomposition).

| $R_f$(EA/MeOH 10:1) = 0.08 | MS (ES) 355(M + H)⁺ |

Examples 2 to 7 were synthesized analogously to Example 1:

EXAMPLE 2

4-(6-Quinaldinyloxy)-3-methylsulfonylbenzyl-oxycarbonylguanidine, dihydrochloride

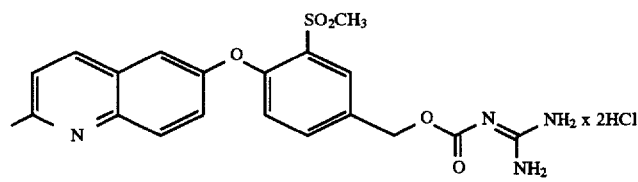

$R_f$ (EA/MeOH 3:1)=0.25 MS (ES): 429 (M+H)⁺

EXAMPLE 3

4-(6-Quinaldinyloxy)-3-trifluoromethylbenzyl-oxycarbonylguanidine, dihydrochloride

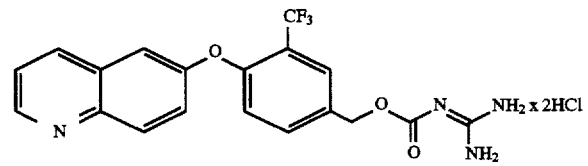

$R_f$ (EA/MeOH 3:1)=0.44 MS (ES) 419 (M+1)⁺

EXAMPLE 4

4-Isopropyl-3-methylsulfonylbenzyloxy-carbonylguanidine, hydrochloride

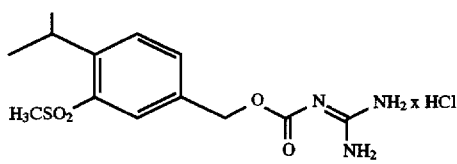

MS (ES): 314 (M+1)⁺

EXAMPLE 5

3-Isopropylbenzyloxycarbonylguanidine, hydrochloride

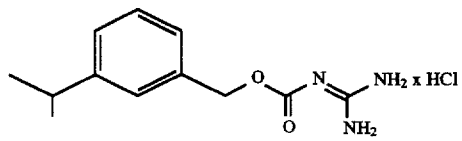

MS (ES) 236 (M+1)⁺

EXAMPLE 6

2-Chloro-5-trifluoromethylbenzyloxycarbonylguanidine, hydrochloride

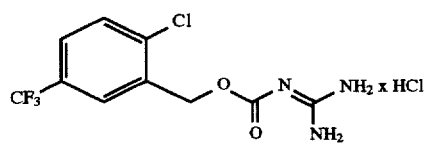

MS (ES): 296 (M+1)⁺

EXAMPLE 7

4-(6-Quinolinyloxy)-3-methylsulfonylbenzyl-oxycarbonylguanidine, dihydrochloride

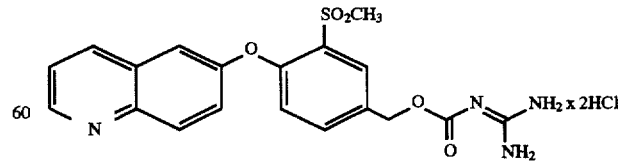

MS (ES): 415 (M+1)⁺

General procedure A: 1 eq. of the appropriate benzylamine in THF (1 ml/mmol) were added dropwise at 0° C. to a solution of carbonyldiimidazole in THF(1.1 eq of CDI, 3 ml/mmol of THF). The reaction solution was stirred at RT (TLC checking) until reaction was complete. 4 eq. of guanidine were then added. After stirring overnight, the THF was distilled off under reduced pressure (in a rotary evaporator), the residue was treated with water and adjusted to pH 6 to 8 with 2N HCl and the corresponding guanidine was filtered off. The benzylaminocarbonylguanidines thus obtained can be converted into the corresponding salt by treating with aqueous, methanolic or ethereal hydrochloric acid or other pharmacologically tolerable acids.

EXAMPLE 8

3-Bromo-5-fluorobenzylaminocarbonylguanidine hydrochloride

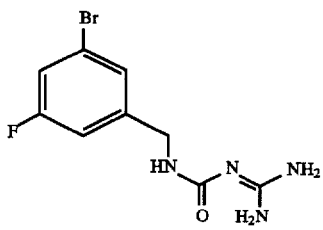

3-Bromo-5-fluorobenzylamine was reacted first with CDI and then with guanidine according to general procedure A and isolated as the hydrochloride.

| M.p.: 125° C. | MS (ES): 289 (M + 1)⁺ |

EXAMPLE 9

3,5-Dimethylbenzylaminocarbonylguanidine hydrochloride

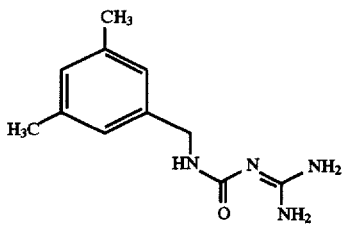

3,5-Dimethylbenzylamine was reacted according to general procedure A and isolated as the hydrochloride.

| M.p.: 97° C. | MS (FAB) 221 (M + 1)⁺ |

EXAMPLE 10

2-Fluorobenzylaminocarbonylguanidine hydrochloride

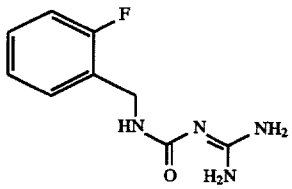

2-Fluorobenzylamine was reacted first with CDI and then with guanidine according to general procedure A and isolated as the hydrochloride.

| M.p.: 125° C. | MS (ES): 211 (M + 1)⁺ |

EXAMPLE 11

3-Fluorobenzylaminocarbonylguanidine hydrochloride

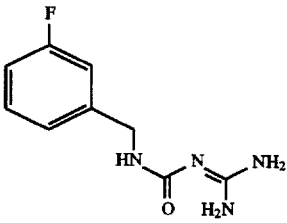

3-Fluorobenzylamine was reacted according to general procedure A and isolated as the hydrochloride (viscous oil).

MS (ES): 211 (M+1)⁺

$R_F$: 0.42 (EA/cyclohexane/methylene chloride/MeOH/ammonia=10:5:5:5:1)

EXAMPLE 12

2,6-Difluorobenzylaminocarbonylguanidine hydrochloride

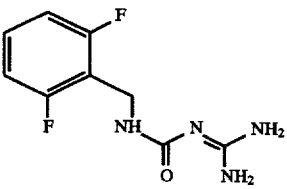

2,6-Difluorobenzylamine was reacted first with CDI and then with guanidine according to general procedure A and isolated as the hydrochloride.

M.p.: 150° C. MS (ES): 229 (M+1)⁺

EXAMPLE 13

2,5-Difluorobenzylaminocarbonylguanidine hydrochloride

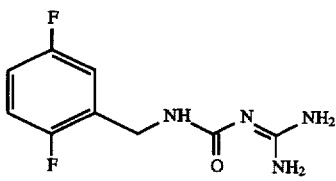

2,5-Difluorobenzylamine was reacted first with CDI and then with guanidine according to general procedure A and isolated as the hydrochloride.

M.p.: 103° C. MS (FAB): 229 (M+1)⁺

EXAMPLE 14

3-Fluoro-5-trifluoromethylbenzylaminocarbonylguanidine hydrochloride

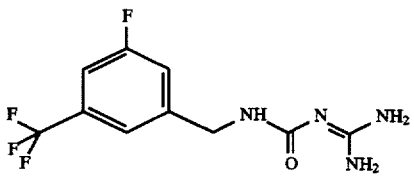

3-Fluoro-5-trifluoromethylbenzylamine was reacted first with CDI and then with guanidine according to general procedure A and isolated as the hydrochloride.

M.p.: 133° C. MS (ES): 279 (M+1)⁺

EXAMPLE 15

4-Dimethylaminobenzylaminocarbonylguanidine hydrochloride

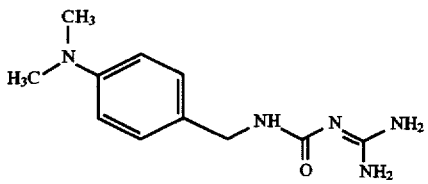

4-Dimethylaminobenzylamine was reacted first with CDI and then with guanidine according to general procedure A and isolated as the hydrochloride.

M.p.: 187° C. MS (ES): 236 (M+1)⁺

EXAMPLE 16

3,5-Difluorobenzylaminocarbonylguanidine hydrochloride

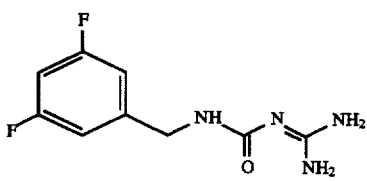

3,5-Difluorobenzylamine was reacted first with CDI and then with guanidine according to general procedure A and isolated as the hydrochloride.

M.p.: 120° C. MS (ES): 229 (M+1)⁺

EXAMPLE 17

3-Methylbenzylaminocarbonylguanidine hydrochloride

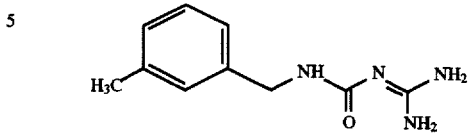

3-Methylbenzylamine was reacted first with CDI and then with guanidine according to general procedure A and isolated as the hydrochloride (viscous hygroscopic oil).

MS (ES): 207 (M+1)⁺

$R_F$: 0.48 (EA/cyclohexane/methylene chloride/MMeOH/ammonia=10:5:5:5:1)

EXAMPLE 18

N-3,5-Difluorobenzyl-N-methylaminocarbonylguanidine hydrochloride

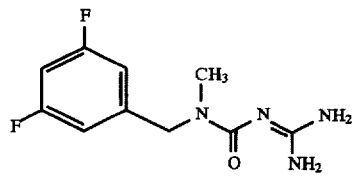

3,5-Difluorobenzylmethylamine (prepared according to standard process: N-formylation, reduction) was reacted first with CDI and then with guanidine according to general procedure A and isolated as the hydrochloride.

M.p. 126° C. MS (ES): 243 (M+1)⁺

EXAMPLE 19

Benzylaminocarbonylguanidine hydrochloride

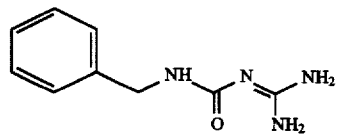

Benzylamine was reacted first with CDI and then with guanidine according to general procedure A and isolated as the hydrochloride.

M.p. 99° C. MS (ES): 193 (M+1)⁺

General procedure B: 1 eq. of the corresponding benzyl alcohol in THF (1 ml/mmol) was added dropwise at 0° C. to a solution of carbonyldiimidazole in THF (1.1 eq of CDI, 3 ml/mmol of THF). The reaction solution was stirred at RT until reaction was complete (usually 30 min). 1.5 eq. of guanidine were then added, the mixture was stirred at RT for a further 1-2 h, the THF was distilled off under reduced pressure (in a rotary evaporator), the residue was treated with water and adjusted to pH 6 to 8 with 2N HCl and the corresponding guanidide was filtered off. The benzyloxycarbonylguanidines thus obtained can be converted into the corresponding salt by treating with aqueous, methanolic or ethereal hydrochloric acid or other pharmacologically tolerable acids.

EXAMPLE 20

3,5-Difluorobenzyloxycarbonylguanidine hydrochloride

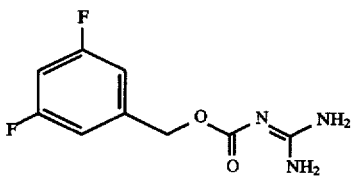

3,5-Difluorobenzyl alcohol was reacted first with CDI and then with guanidine according to general procedure B and isolated as the hydrochloride.

M.p.: 177° C. MS (Cl): 230 (M+1)$^+$

EXAMPLE 21

2,5-Difluorobenzyloxycarbonylguanidine hydrochloride

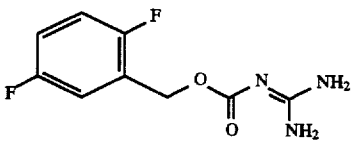

2,5-Difluorobenzyl alcohol was reacted first with CDI and then with guanidine according to general procedure B and isolated as the hydrochloride.

M.p.: 169° C. MS (ES): 230 (M+1)$^+$

EXAMPLE 22

2,3,6-Trifluorobenzyloxycarbonylguanidine hydrochloride

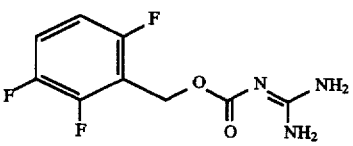

2,3,6-Trifluorobenzyl alcohol was reacted first with CDI and then with guanidine according to general procedure B and isolated as the hydrochloride.

M.p.: 180° C. MS (ES): 248 (M+1)$^+$

EXAMPLE 23

N-(3,4-Dichlorobenzyl)-N-methylaminocarbonylguanidine hydrochloride

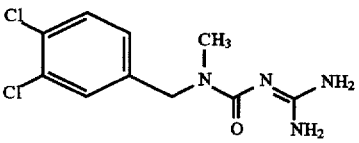

3.5 g of CDI were added to a solution of 3.0 g of 3,4-dichlorobenzylmethylamine in 110 ml of THF and it was stirred at RT overnight. After addition of 4.6 g of guanidine, the reaction mixture was again stirred overnight and concentrated on a rotary evaporator, and the residue was stirred with 120 ml of water. The precipitate which was deposited during this process was filtered off with suction, dried in vacuo and dissolved in 50 ml of ethyl acetate and 7 ml of methanol. After addition of ethereal hydrochloric acid and suction filtration of the precipitated product, 3.8 g of N-(3,4-dichlorobenzyl)-N-methylaminocarbonylguanidinehydrochloride were obtained;

m.p.: 198°–199° C.

$^1$H-NMR (DMSO-d6): δ {ppm}=3.05 (3H), 4.6 (2H), 7.3 (1H), 7.6 (1H), 7.7 (1H), 8.25 (2H), 8.65 (2H), 10.7 (1H).

EXAMPLE 24

N-(2-Chloro-5-trifluoromethylbenzyl)-N-methylamincarbonyluanidine hydrochloride

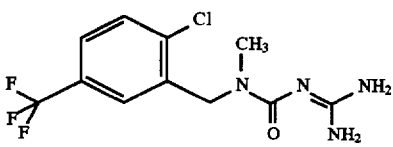

a) 2.1 g of 2-chloro-5-trifluoromethylbenzaldehyde, 15 ml of methylamine and 2 g of magnesium sulfate were stirred at room temperature for 2 h, the excess methylamine for the most part evaporating. The reaction mixture was diluted with ether, filtered and concentrated in vacuo. The methylbenzimine thus obtained was dissolved in 15 ml of THF and added dropwise to a suspension of 1.5 g of sodium borohydride in 15 ml of THF. After stirring overnight, the mixture was treated with 30 ml of methanol, stirred for a further 30 min and then rendered acidic with dil. hydrochloric acid. It was extracted with tert-butyl methyl ether, and the aqueous phase was rendered alkaline and extracted twice again with tert-butyl methyl ether. After concentrating this extract, 1.0 g of N-(2-chloro-5-trifluoromethylbenzyl)-N-methylamine was obtained.

b) 1.0 g of N-(2-chloro-5-trifluoromethylbenzyl)-N-methylamine was reacted with 0.75 g of CDI and 1.1 g of guanidine analogously to Example 23. 0.6 g of N-(2-chloro-5-trifluoromethylbenzyl)-N-methylaminocarbonylguanidine hydrochloride is obtained;

m.p. 178°–179° C.

$^1$H-NMR (DMSO-d6): δ {ppm}=3.1 (3H), 4.7 (2H), 7.6 (1H), 7.75 (2H), 8.2 (2H), 8.6 (2H), 10.6 (1H).

EXAMPLE 25

N-Methyl-N-(3-methylsulfonyl-4-phenoxybenzyl) aminocarbonylguanidine methanesulfonate

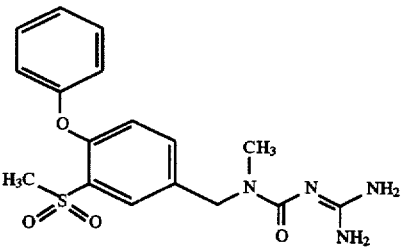

a) Starting from 4-phenoxy-3-methylsulfonylbenzoic acid (according to EP-OS 589 336-HOE 92/F 303), by reduction to the alcohol and subsequent manganese dioxide oxidation 4-phenoxy-3-methylsulfonylbenzaldehyde was obtained, which was converted by reaction with methylamine and subsequent reduction with sodium borohydride as described in Example 24 a into N-methyl-N-(3-methylsulfonyl-4-phenoxybenzyl)amine.

b) 1.0 g of N-methyl-N-(3-methylsulfonyl-4-phenoxybenzyl)amine and 0.7 g of CDI dissolved in 25 ml of THF were stirred at RT for 2 h. 1.1 g of guanidine were added, the mixture was stirred overnight and the solvent was distilled off on a rotary evaporator. The residue was taken up in 100 ml of water, adjusted to pH 7.6 with 10 percent hydrochloric acid and extracted twice with ethyl acetate. After concentrating, the guanidine derivative obtained was dissolved again in ethyl acetate, and by adding the equivalent amount of methanesulfonic acid was precipitated as the methanesulfonate. 0.8 g of N-methyl-N-(3-methylsulfonyl-4-phenoxybenzyl)aminocarbonylguanidine methanesulfonate was obtained;

m.p.: 209°–210° C.

$^1$H-NMR (DMSO-d6): δ {ppm}=2.35 (3H), 3.0 (3H), 3.4 (3H), 4.6 (2H), 7.0–7.9 (8H), 8.1 (4H), 9.7 (1H).

EXAMPLE 26

N-Methyl-N-(3-methylsulfonyl-4-isopropylbenzyl) aminocarbonylguanidine methanesulfonate

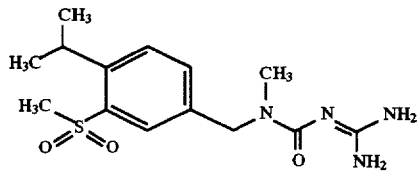

Starting from 4-isopropyl-3-methylsulfonylbenzoic acid in the manner described in Example 25, N-Methyl-N-(3-methylsulfonyl-4-isopropylbenzyl)aminocarbonylguanidine methanesulfonate was obtained;

m.p.: 180° C.

$^1$H-NMR (DMSO-d6): δ {ppm}=1.3 (6H), 2.4 (3H), 3.0 (3H), 3.25 (3H), 3.8 (1H), 4.6 (2H), 7.6 (1H), 7.7 (1H), 7.8 (1H), 8.15 (4H), 9.8 (1H).

EXAMPLE 27

N-(4-Fluoro-3-trifluoromethylbenzyl)-N-methylaminocarbonylguanidine hydrochloride

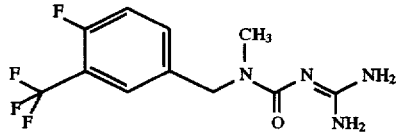

a) 1.9 g of 4-fluoro-3-trifluoromethylbenzaldehyde, 30 ml of methylamine and 2 g of magnesium sulfate were stirred at room temperature for 2 h, the excess methylamine for the most part evaporating. The reaction mixture was diluted with ether, filtered and concentrated in vacuo. The methylbenzimine thus obtained was dissolved in 30 ml of methanol and, after addition of 2.0 g of sodium borohydride, the mixture was stirred overnight. It was concentrated in vacuo, and the residue was treated with 20 ml of 10 percent hydrochloric acid and extracted twice with tert-butyl methyl ether. The aqueous phase was then rendered alkaline and extracted twice again with tert-butyl methyl ether. After concentrating these extracts, 1.0 g of N-(4-fluoro-3-trifluoromethylbenzyl)-N-methylamine was obtained.

b) 1.0 g of N-(4-fluoro-3-trifluoromethylbenzyl)-N-methylamine and 1.0 g of CDI were stirred for 2 h in THF. 1.4 g of guanidine were then added, and the mixture was stirred overnight, concentrated on a rotary evaporator and stirred with water. The precipitate which was deposited was filtered off with suction and converted into the hydrochloride using ethyl acetate/HCl. 1.2 g of N-(4-fluoro-3-trifluoromethylbenzyl)N-methylaminocarbonylguanidine hydrochloride are obtained;

m.p.: 150°–152° C.

$^1$H-NMR (DMSO-d6): δ {ppm}=3.05 (3H), 4.65 (2H), 7.5 (1H), 7.7 (2H), 8.2 (2H), 8.6 (2H), 10.5 (1H).

EXAMPLE 28

4-Isopropyl-3-methylsulfonylbenzyloxycarbonylguanidine hydrochloride

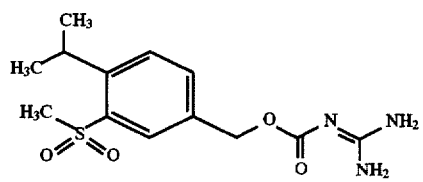

Synthesis route:

a) 4-Isopropylbenzoic acid by oxidation of 4-isopropylbenzaldehyde with sodium perborate in acetic acid at 50° C., m.p. 118° C.

b) 4-Isopropyl-3-chlorosulfonylbenzoic acid from a) by heating in chlorosulfuric acid at 95° C. for 3 h, m.p. 203°–4° C.

c) 2-Isopropyl-5-carboxybenzenesulfinic acid from b) by reduction with sodium sulfite at 60° C. in aqueous sodium hydroxide solution (pH ~9–10), m.p. 205°–7° C.

d) 4-Isopropyl-3-methylsulfonylbenzoic acid from c) by alkylation with methyl bromide in the presence of NaOH in DMF at 60° C. for 3 h, m.p. 209°–11° C.

e) 2.3 g of ethyl chloroformate dissolved in 5 ml of THF were added dropwise at −10° C. to a solution of 4.8 g of 4-isopropyl-3-methylsulfonylbenzoic acid and 2.1 g of triethylamine in 40 ml of THF. After stirring for 1 hour, the precipitate which was deposited was filtered off with suction, and the filtrate was added dropwise to a solution of 2.3 g of sodium borohydride in 25 ml of water. The reaction mixture was subsequently stirred for 5 h, acidified with hydrochloric acid and extracted with ether, and the organic phase was washed with 10 percent sodium hydroxide solution. After concentrating, 3.1 g of 4-isopropyl-3-methylsulfonylbenzyl alcohol were obtained.

f) 2.3 g of 4-isopropyl-3-methylsulfonylbenzyl alcohol and 1.95 g of CDI are stirred at RT overnight in 50 ml of DMF 3 g of guanidine were added, and the reaction mixture was stirred for 4 h and then concentrated on a rotary evaporator. The residue was poured onto 250 ml of water, and after stirring for 1 hour the crystalline product was filtered off with suction. After conversion into the hydrochloride, 1.5 g of 4-isopropyl-3-methylsulfonylbenzyloxycarbonylguanidine hydrochloride were obtained;

m.p.: 159°–160° C.

$^1$H-NMR (DMSO-d6): δ {ppm}=1.3 (6H), 3.3 (3H), 3.8 (1H), 5.3 (2H), 7.75 (2H), 7.95 (1H), 8.1 (2H), 8.5 (2H), 11.6 (1H).

EXAMPLE 29

3-Methylsulfonyl-4-phenoxybenzyloxycarbonylguanidine methanesulfonate

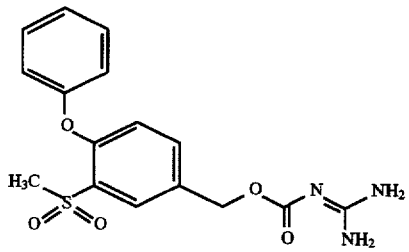

Analogously to Example 28, starting from 3-methylsulfonyl-4-phenoxybenzoic acid, 3-methylsulfonyl-4-phenoxybenzyloxycarbonylguanidine methanesulfonate was obtained;

m.p.: 177° C.

$^1$H-NMR (DMSO-d6): δ {ppm}=2.35 (3H), 3.4 (3H), 5.3 (2H), 7.05 (1H), 7.15 (2H), 7.3 (1H), 7.5 (2H), 7.75 (1H), 7.9 (2H), 8.0 (1H), 8.2 (2H), 11.3 (1H).

a. 4-Chloro-3-chlorosulfonylbenzoic acid 28.05 kg (16 l) of chlorosulfonic acid are initially introduced and 4.4 kg of 4-chlorobenzoic acid were added in the course of 10 minutes with stirring (no heat effect). In the course of 90 minutes, the mixture was heated to 130°–135° C., during which evolution of HCl was to be observed. The mixture was subsequently stirred for 3 hours at the stated temperature, and allowed to cool and to stand overnight. The reaction mixture was then allowed to run with stirring onto a mixture of 70 kg of ice and 30 kg of water, during which the temperature must not climb above 10° C. The product was filtered off with suction, washed with 40 kg of water and dried in vacuo at 40° C.

Yield: 6.2 kg (86.5%) of crude product which was reacted further without further purification.

b. 4-Chloro-3-hydroxysulfinylbenzoic acid 157.55 g of sodium sulfite (1.25 mol) were dissolved in 725 ml of water and heated to 70° C. At this temperature, 255.08 g of 5-carboxy-2-chlorobenzenesulfonyl chloride were added in portions, the pH (electrode) being kept between 8 and 10 by continuous addition of 320 ml of half-concentrated sodium hydroxide solution (the reaction is slightly exothermic). After the end of the addition, the mixture was subsequently stirred at 70° C. for 2 hours. As soon as the reaction had ended, 5 g of active carbon were added, and after 30 minutes the mixture was filtered hot through a clarifying layer and diluted with 600 ml of water. The solution was allowed to cool to 15°–20° C. and was adjusted to pH 0 using 250 ml of conc. hydrochloric acid, the viscous suspension was stirred in an ice bath for a further 30 minutes and the mixture was then stood well closed in a refrigerator over the weekend. The precipitate was filtered off with suction, washed once with 100 ml of 2N hydrochloric acid and then sucked dry in a stream of air. The substance was sucked dry in vacuo at 50° C.

Yield: 280 g of crude product which owing to the high concentration still contains salts which coprecipitate. The product was reacted without further purification.

c. 4-Chloro-3-hydroxysulfinylbenzoic acid, disodium salt 80.0 g of NaOH pellets (2 mol) were dissolved in 250 ml of water, diluted with 250 ml of methanol and 220 g of 5-carboxy-2-chlorosulfinic acid (1 mol) were added in portions. The reaction mixture was subsequently stirred at RT for 3 hours and filtered off with suction through a clarifying layer, and the filtrate was concentrated. The residue was taken up in 500 ml of acetone, thoroughly stirred and filtered off with suction. The precipitate was slurried 4 times using about 200 ml of acetone each time and again sucked dry. The disodium salt was dried in vacuo at 50° C.

Yield: 260 g of crude product which still contains excess sodium hydroxide. The product was reacted without further purification.

d. Methyl 4-chloro-3-methylsulfonylbenzoate 250 g of disodium 4-chloro-3-hydroxysulfinylbenzoate were suspended in 500 ml of abs. dimethylformamide at RT, 218 ml of methyl iodide (3.5 mol) were added and the reaction mixture was heated to 60° C. It was subsequently stirred at this temperature for 4 hours, then allowed to stand at RT overnight. The mixture became solid on cooling. It was warmed to 70° C., diluted with 250 ml of abs. dimethylformamide and subsequently stirred at 70° C. for a further 3 hours. The solvent was distilled off, the residue was taken up in 1000 ml of water, stirred for 30 minutes in an ice bath, filtered off with suction and washed 3 times with about 200 ml of water each time, sucked dry and dried in vacuo (50° C.).

Crude yield: 175.2 g (0.7 mol)

The product was recrystallized from ethanol.

Yield: 171.5 g e. 4-Phenoxy-3-methylsulfonylbenzoic acid 65.9 g of phenol (0.7 mol) were dissolved in 340 ml of abs. dimethylformamide at RT, under argon, 269.6 g of ground and dried potassium carbonate (1.95 mol) were added and the mixture was stirred at RT for one hour. 161.6 g of methyl 4-chloro-3-methylsulfonylbenzoate (0.65 mol) in 340 ml of abs. dimethylformamide were then added and the mixture was stirred under reflux (150° C.) for 14 hours. The solvent was distilled off, and the residue was taken up in 1500 ml of water, cautiously rendered acidic with conc. hydrochloric acid (it foams), allowed to stand at RT overnight and then filtered off with suction. The precipitate was washed 3 times with about 200 ml of 1N hydrochloric acid each time and dried.

Crude yield: 185.4 g

The precipitate was dissolved in 1000 ml of dioxane, a solution of 24 g of NaOH (0.6 mol) in 300 ml of water was added and the mixture was stirred at RT for 3 hours. The dioxane was distilled off, the residue was dissolved in 1300 ml of water, the solution was rendered acidic with 2N hydrochloric acid and stirred for 30 minutes, and the precipitate was filtered off with suction and dried.

Final weight: 176.7 g (93% of theory)

M.p.: 182°–184° C.

EXAMPLE 30

2-Chloro-5-trifluoromethylbenzyloxycarbonylguanidine hydrochloride

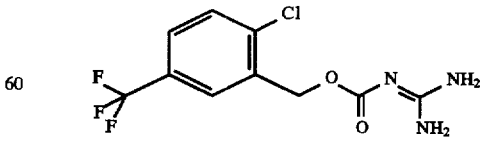

Analogously to Example 28, starting from 2-chloro-5-trifluoromethylbenzoic acid, 2-chloro-5-trifluoromethylbenzyloxycarbonylguanidine hydrochloride was obtained;

m.p.: 170° C.

¹H-NMR (DMSO-d6): δ {ppm}=5.4 (2H), 7.8 (2H), 7.95 (1H), 8.15 (2H), 8.65 (2H), 11.9 (1H).

EXAMPLE 31

3-Isopropylbenzyloxycarbonylguanidine hydrochloride

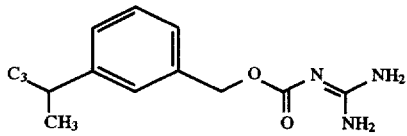

a. 3-Isopropylphenyl trifluoromethanesulfonate 100 g of 3-isopropylphenol were dissolved in 1 l of $CH_2Cl_2$ and first 95 g of lutidine, then 18 g of 4-dimethylaminopyridine, were added at −30° C. 150 ml of trifluoromethanesulfonic anhydride were then slowly added dropwise at this temperature. The reaction mixture was warmed to RT, poured onto 2 l of a saturated aqueous $NaHCO_3$ solution, and the $CH_2Cl_2$ was separated off and extracted a further 2 times with 300 ml of the same solvent. The extract was dried over $Na_2SO_4$ and the solvent was removed in vacuo. Chromatography on silica gel using EA/HEP 1:8 yields 181 g of a colorless oil.

$R_f$ (EA/HEP 1:8)=0.56 b. Methyl 3-isopropylbenzoate 180 g of 3-isopropylphenyl trifluoromethanesulfonate were dissolved in 340 ml of methanol and 670 ml of DMF, 187 ml of triethylamine, 1.5 g of Pd(ll) acetate and 2.8 g of 1,3-bis(diphenylphosphino)propane were added and the mixture was heated to reflux for 8 h under a CO atmosphere. The solvents were then removed in vacuo, and the residue was taken up using 1 l of a saturated aqueous $NaHCO_3$ solution and 1 l of water and extracted 3 times using 500 ml of MTB each time. The extract was dried over $Na_2SO_4$ and the solvent was removed in vacuo. Chromatography on silica gel using EA/HEP 1:8 yields 25 g of a colorless oil.

$R_f$ (EA/HEP 1:8)=0.22 c. 0.8 g of 3-isopropylbenzyl alcohol was obtained from 1.0 g of methyl 3-isopropylbenzoate by reduction with lithium aluminum hydride.

d. From 0.7 g of 3-isopropylbenzyl alcohol, 1 g of CDI and 1.3 g of guanidine, analogously to Example 28 b, 0.6 g of 3-isopropylbenzyloxyarbonylguanidine hydrochloride was obtained;

m.p.: 112° C.

¹H-NMR (DMSO-d6): δ {ppm}=1.2 (6H), 2.9 (1H), 5.2 (2H), 7.3 (4H), 8.15 (2H), 8.55 (2H), 11.65.

EXAMPLE 32

4-(6-Quinolyloxy)-3-methylsulfonylbenzyloxycarbonyl-guanidine hydrochloride

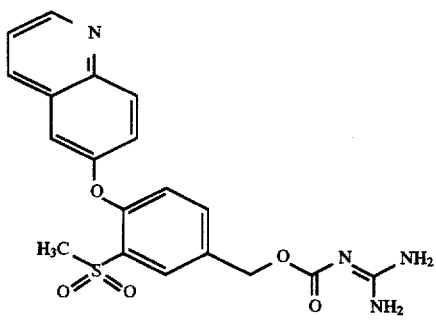

Analogously to Example 24, starting from methyl 4-(6-quinolyloxy)-3-methylsulfonylbenzoate, 4-(6-quinolyloxy)-3-methylsulfonylbenzyloxycarbonylguanidine hydrochloride was obtained; m.p.: 170° C.

a. Methyl 4-(6-quinolyloxy)-3-methylsulfonylbenzoate 2 mmol of methyl 4-chloro-3-methylsulfonylbenzoate, 2 mmol of 6-hydroxyquinoline and 6 mmol of $K_2CO_3$ were stirred at 130° C. for 2 h in 20 ml of DMF (anhydrous). The mixture was then poured into 100 ml of saturated aqueous $NaHCO_3$ solution and extracted 3 times with 100 ml of EA. The extract was dried over $Na_2SO_4$, the solvent was removed in vacuo and the product was reacted further without further purification.

$R_f$ (MTB)=0.15 MS (DCI): 358 $(M+1)^+$

EXAMPLE 33

3-Trifluoromethyl-4-methoxybenzyloxycarbonylguanidine hydrochloride

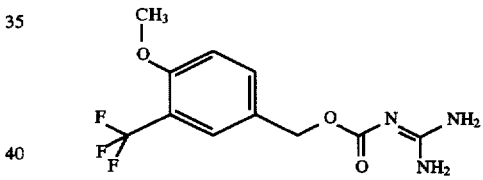

a) 9.7 g of methyl 3-iodo-4-methoxybenzoate, 9.4 g of potassium trifluoroacetate and 12.9 g of copper(I) iodide were heated at 160° C. for 5 h in 250 ml of DMF. The mixture was poured onto 500 ml of $NaHCO_3$ solution, the precipitate which was deposited was filtered off and both the precipitate and the aqueous phase were extracted with ethyl acetate. The combined organic phases were concentrated, and the residue was purified by flash chromatography using hexane/ethyl acetate 3:1. 6 g of methyl 3-trifluoromethyl-4-methoxybenzoate were obtained;

m.p.: 77°–79° C.

b) The methyl 3-trifluoromethyl-4-methoxybenzoate was converted analogously to Example 31 into 3-trifluoromethyl-4-methoxybenzyloxycarbonylguanidine hydrochloride;

m.p.: 143°–144° C.

¹H-NMR (DMSO-d6): δ {ppm}=3.9 (3H), 5.25 (2H), 7.3 (1H), 7.75 (2H), 8.1 (2H), 8.5 (2H), 11.6 (1H).

Pharmacological data:

Inhibition of the $Na^+/H^+$ exchanger of rabbit erythrocytes

New Zealand White rabbits (Ivanovas) received a standard diet containing 2% cholesterol for six weeks in order to activate the $Na^+/H^+$ exchange and thus to be able to determine, by flame photometry, the $Na^+$ influx into the erythrocytes via Na⁺/H⁺ exchange. The blood was removed from the aural arteries and rendered incoagulable using 25 IU of potassium heparin. A part of each sample was used for the duplicate determination of the hematocrit by means of centrifugation. Aliquots of in each case 100 µl were used for measuring the initial Na⁺ content of the erythrocytes.

In order to determine the amiloride-sensitive sodium influx, 100 µl of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris(hydroxymethyl) aminomethane). The erythrocytes were then washed three times with ice-cold $MgCl_2$/ouabain solution (mmol/l: 112 $MgCl_2$, 0.1 ouabain) and hemolyzed in 2.0 ml of distilled water. The intracellular sodium content was determined by flame photometry.

The net influx of Na⁺ was calculated from the difference between the initial sodium values and the sodium content of the erythrocytes following incubation. The amiloride-inhibitable sodium influx was calculated from the difference in the sodium content of the erythrocytes following incubation with and without amiloride $3 \times 10^{-4}$ mol/l. This method was also employed in the case of the compounds according to the invention.

Results

Inhibition of the Na⁺/H⁺ exchanger:

| Example | $IC_{50}$ (µmol/l) |
|---------|---------------------|
| 1       | <1                  |

We claim:
1. A compound of the formula I

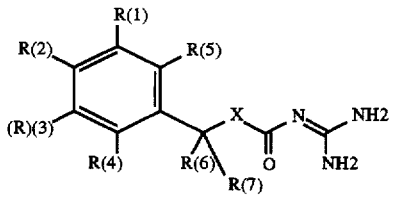

in which:
R(1), R(2) and R(3) independently of one another are —Y—{4—R(8)-phenyl}, —Y—{3—R(8)-phenyl} or —Y—{2—R(8)-phenyl}, where the phenyl in each case is unsubstituted or substituted by 1–2 substituents selected from the group consisting of F, Cl, —CF₃, methyl, hydroxyl, methoxy and —NR(96)R(97); R(96) and R(97) independently of one another are hydrogen or —CH₃;
Y is a bond, CH₂, oxygen, —S— or —NR(9); R(9) is hydrogen or alkyl having 1, 2, 3 or 4 carbon atoms;
R(8) is $SO_a\{NR(98)\}_bNR(99)R(10)$;
a is 1 or 2;
b is 0 or 1;
a+b=2;
R(98), R(99) and R(10) independently of one another are hydrogen, —(C₁-C₈)-alkyl, benzyl, —(C₂-C₈)-alkylene—NR(11)R(12), (C₂-C₈)-alkylene—NR(13)—(C₂-C₈)-alkylene—NR(37)R(38) or (C₀-C₈)-alkylene—CR(39)R(40)—CR(41)R(42)(C₀-C₈)-alkylene—NR(43)R(44); R(11), R(12), R(13), R(37), R(38), R(43) and R(44) independently of one another are hydrogen, —(C₁-C₈)-alkyl or benzyl; R(39), R(40), R(41) and R(42) independently of one another are hydrogen, —(C₁-C₈)-alkyl or —(C₀-C₃)-alkylenephenyl, where the phenyl is unsubstituted or substituted by 1–3 substituents selected from the group consisting of F, Cl, —CF₃, methyl and methoxy;

or

R(99) and R(10) together are 4–6 methylene groups, of which one CH₂ group can be replaced by oxygen, —S—, —NH—, —NCH₃ or —N-benzyl;

or

R(8) is $SO_a\{NR(98)\}_bNR(95)—C\{=N—R(94)\}—NR(93)R(92)$; R(92), R(93), R(94) and R(95) independently of one another are hydrogen or alkyl having 1, 2, 3 or 4 carbon atoms;

or

R(1), R(2) and R(3) independently of one another are pyrrol-1-yl, pyrrol-2-yl or pyrrol-3-yl, which are unsubstituted or substituted by 1–4 substituents selected from the group consisting of F, Cl, Br, I, —CN, (C₂-C₈)-alkanoyl, (C₂-C₈)-alkoxycarbonyl, formyl, carboxyl, —CF₃, methyl, and methoxy;

or

R(1), R(2) and R(3) independently of one another are hydrogen, —(C₁-C₈)-alkyl, —(C₂-C₈)-alkenyl or —(CH₂)ₘR(14);
m is zero, 1 or 2;
R(14) is —(C₁-C₈)-cycloalkyl or phenyl, which is unsubstituted or substituted by 1–3 substituents selected from the group consisting of F, Cl, —CF₃, methyl, methoxy and —NR(15)R(16); R(15) and R(16) are hydrogen or —CH;

or

R(1), R(2) and R(3) independently of one another are —Q—4—{(CH₂)ₖ—CHR—(17)(C=O)R(20)-1-phenyl, —Q—3—{(CH₂)ₖ—CHR(17)—(C=O) R(20)}-phenyl or —Q—2—{(CH₂)ₖ—CHR(17)—(C=O)R(20)}-phenyl, where the phenyl in each case is unsubstituted or substituted by 1–2 substituents selected from the group consisting of F, Cl, —CF₃, methyl, hydroxyl, methoxy and —NR(35)R(36); R(35) and R(36) independently of one another are hydrogen or —CH₃;
Q is a bond, oxygen, —S— or —NR(18); R(18) is hydrogen or —(C₁-C₄)-alkyl;
R(17) is —OR(21) or —NR(21)R(22); R(21) and R(22) independently of one another are hydrogen, —(C₀-C₈)-alkyl, —(C₁-C₈)-alkanoyl, —(C₁-C₈)-alkoxycarbonyl, benzyl, or benzyloxycarbonyl;

or

R(21) is trityl;
R(20) is —OR(23) or —NR(23)R(24); R(23), R(24) independently of one another are hydrogen, —(C₁-C₈)-alkyl or benzyl;
k is zero, 1, 2, 3 or 4;

or

R(1), R(2) and R(3) independently of one another are (C₁-C₉)-heteroaryl, which is linked via C or N and which is unsubstituted or substituted by 1–3 substituents selected from the group consisting of F, Cl, CF₃, CH₃, methoxy, hydroxyl, amino, methylamino and dimethylamino;

or

R(1), R(2) and R(3) are —SR(25), —OR(25), —NR(25) R(26), —CR(25)R(26)R(27);
R(25) is —$C_jH_{2j}$ (C₁-C₉)-heteroaryl, which is unsubstituted or substituted by 1–3 substituents selected from the group consisting of F, Cl, CF$_3$, CH$_3$, methoxy, hydroxyl, amino, methylamino and dimethylamino;

f is zero, 1 or 2;

R(26) and R(27) independently of one another are R(25), hydrogen or (C$_1$-C$_4$)-alkyl;

or

R(1), R(2) and R(3) independently of one another are (C$_1$-C$_9$)-heteroaryl N-oxide, which is linked via C or N and which is unsubstituted or substituted by 1–3 substituents selected from the group consisting of F, Cl, CF$_3$, CH$_3$, methoxy, hydroxyl, amino, methylamino and dimethylamino;

or

R(1), R(2) and R(3) independently of one another are —SR(28), —OR(28), —NR(28)R(29) or —CR(28)R(29)R(30);

R(28) is —C$_g$H$_{2g}$—(C$_1$-C$_9$)-heteroaryl N-oxide, which is unsubstituted or substituted by 1–3 substituents selected from the group consisting of F, Cl, CF$_3$, CH$_3$, methoxy, hydroxyl, amino, methylamino and dimethylamino;

g is zero, 1 or 2;

R(29), R(30) independently of one another are defined as R(28), or are hydrogen or (C$_1$-C$_4$)-alkyl;

or

R(1), R(2) and R(3) independently of one another are hydrogen, F, Cl, Br, I, —C≡N, T—(CH$_2$)$_h$—(C$_i$F$_{2i+1}$), R(31)SO$_l$—, R(32)R(33)N—CO—, R(34)—CO— or R(45)R(46)N—SO$_2$, where the perfluoroalkyl group is straight-chain or branched;

T is a bond, oxygen, —S— or —NR(47);

l is zero, 1 or 2;

h is zero, 1 or 2;

i is 1, 2, 3, 4, 5 or 6;

R(31), R(32), R(34) and R(45) independently of one another are —(C$_1$-C$_8$)-alkyl, —(C$_3$-C$_6$)-alkenyl, (CH$_2$)$_n$R(48) or —CF$_3$;

n is zero, 1, 2, 3 or 4;

R(47) is hydrogen or alkyl having 1,2 or 3 carbon atoms;

R(48) is —(C$_3$-C$_7$)-cycloalkyl or phenyl, which is unsubstituted or substituted by 1–3 substituents selected from the group consisting of F, Cl, —CF$_3$, methyl, methoxy and —NR(49)R(50);

R(49) and R(50) are hydrogen or alkyl having 1, 2, 3 or 4 carbon atoms;

or

R(32), R(34) and R(45) are hydrogen;

R(33) and R(46) independently of one another are hydrogen or alkyl having 1, 2, 3 or 4 carbon atoms;

or

R(32) and R(33) and also R(45) and R(46) together are 5 or 6 methylene groups, of which one CH$_2$ group can be replaced by oxygen, —S—, —NH—, —NCH$_3$ or —N-benzyl;

or

R(1), R(2) and R(3) independently of one another are R(51)—A—G—D—;

R(51) is a basic protonatable radical, selected from the group consisting of an amino group —NR(52)R(53), an amidino group R(52)R(53)N—C{=N—R(54)} and a guanidino group R(52)R(53)N—C{=N—R(54)}—NR(55)—;

R(52), R(53), R(54) and R(55) independently of one another are hydrogen or alkyl having 1, 2, 3 or 4 carbon atoms;

or

R(52) and R(53) are a group C$_\alpha$H$_{2\alpha}$;

α is 4, 5, 6 or 7;

where if α=5, 6 or 7 a carbon atom of the group C$_\alpha$H$_{2\alpha}$ can be replaced by a heteroatom group O, SO$_d$ or NR(56);

or

R(53) and R(54), or R(54) and R(55), or R(52) and R(55) are a group C$_\gamma$H$_{2\gamma}$;

γ is 2, 3, 4 or 5;

where if γ=3, 4 or 5 a carbon atom of the group C$_\gamma$H$_{2\gamma}$ can be replaced by a heteroatom group O, SO$_d$ or NR(56);

d is zero, 1 or 2;

R(56) is hydrogen or methyl;

or

R(51) is a basic heteroaromatic ring system having 1–9 carbon atoms;

A is a group C$_e$H$_{2e}$;

e is zero, 1, 2, 3, 4, 5, 6, 7, 8, 9 or 10;

where in the group C$_e$H$_{2e}$ a carbon atom can be replaced by one of the groups —O—, —CO—, —CH{OR(57)}—, —SO$_r$—, —NR(57)—, —NR(57)—CO—, —NR(57)—CO—NH—, —NR(57)—CO—NH—SO$_2$— or —NR(57)—SO$_2$—;

r is zero, 1 or 2;

G is a phenylene radical

R(58) and R(59) independently of one another are hydrogen, methyl, methoxy, F, Cl, Br, I, CF$_3$ or —SO$_s$—R(60);

s is zero, 1 or 2;

R(60) is methyl or NR(61)R(62); R(61) and R(62) independently of one another are hydrogen or alkyl having 1, 2, 3 or 4 carbon atoms;

D is —C$_v$H$_{2v}$—E$_w$—;

v is zero, 1, 2, 3 or 4;

E is —O—, —CO—, —CH{OR(63)}—, —SO$_{aa}$— or —NR(63)—;

w is zero or 1;

aa is zero, 1 or 2

R(63) is hydrogen or methyl;

or

R(1), R(2) and R(3) independently of one another are —CF$_2$R(64), —CF{R(65)}{R(66)}, —CF{(CF$_2$)$_q$—CF$_3$}{R(65)}, —C{(CF$_2$)$_p$—CF$_3$}=CR(65) R(66);

R(64) is alkyl having 1, 2, 3 or 4 carbon atoms or cycloalkyl having 3, 4, 5, 6 or 7 carbon atoms; R(65) and R(66) independently of one another are hydrogen or alkyl having 1, 2, 3, or 4 carbon atoms;

q is zero, 1 or 2;

p is zero, 1 or 2;

or

R(1), R(2) and R(3) independently of one another are —OR(67) or —NR(67)R(68);

R(67) and R(68) independently of one another are hydrogen or alkyl having 1, 2, 3, 4, 5 or 6 carbon atoms;

or

R(67) and R(68) together are 4, 5, 6 or 7 methylene groups, of which one $CH_2$ group can be replaced by oxygen, —S—, $SO_2$, —NH—, —$NCH_3$ or —N-benzyl;

R(4) and R(5) independently of one another are hydrogen, alkyl having 1, 2, 3 or 4 carbon atoms, F, Cl, —OR(69), —NR(70)R(71) or —$C_zF_{2z+1}$; R(69), R(70) and R(71) independently of one another are hydrogen or alkyl having 1, 2 or 3 carbon atoms;

z is 1, 2, 3 or 4;

R(6) and R(7) independently of one another are hydrogen or alkyl having 1, 2, 3 or 4 carbon atoms;

x is oxygen;

or a pharmaceutically tolerable salt of the said compound; but where compounds are excluded in which the radicals R(1) to R(7) are simultaneously equal to hydrogen.

2. A compound of the formula I as claimed in claim 1, wherein:

R(1), R(2) and R(3) independently of one another are —Y—{4—R(8)-phenyl}, —Y—{3—R(8)-phenyl} or —Y—{2—R(8)-phenyl}, where the phenyl is in each case unsubstituted or substituted by a substituent from the group consisting of F, Cl, —$CF_3$, methyl, methoxy and —NR(96)R(97); R(96) and R(97) independently of one another are hydrogen or —$CH_3$;

Y is a bond, oxygen, —S— or —NR(9); R(9) is hydrogen or methyl;

R(8) is $SO_a${NR(98)}$_b$NR(99)R(10);

a is 1 or 2;

b is 0 or 1;

a+b=2;

R(98) is hydrogen, alkyl having 1, 2, 3, 4 or 5 carbon atoms or benzyl; R(99) and R(10) independently of one another are hydrogen, alkyl having 1 or 2 carbon atoms, benzyl, —$(C_2-C_3)$-alkylene—NR(11)R(12), $(C_2-C_3)$-alkylene—NR(13)—$(C_2-C_3)$-alkylene—NR(37)R(38) or —$(C_0-C_2)$-alkylene—CR(39)R(40)—CR(41)R(42)$(C_0-C_2)$-alkylene—NR(43)R(44); R(11), R(12), R(13), R(37), R(38), R(43) and R(44) independently of one another are hydrogen, methyl or ethyl; R(39), R(40), R(41) and R(42) independently of one another are hydrogen, alkyl having 1, 2, 3 or 4 carbon atoms or benzyl, where the phenyl is unsubstituted or substituted by a substituent selected from the group consisting of F, Cl, —$CF_3$, methyl and methoxy;

or

R(99) and R(10) together are 4, 5 or 6 methylene groups, of which one $CH_2$ group can be replaced by oxygen, —S—, —NH— or —$NCH_3$;

or

R(8) is $SO_a${NR(98)}$_b$NR(95)-C{=N-R(94)}—NR(93)R(92); R(95) is hydrogen; R(92), R(93) and R(94) independently of one another are hydrogen or alkyl having 1, 2, 3 or 4 carbon atoms;

or

R(1), R(2) and R(3) independently of one another are pyrrol-1-yl, pyrrol-2-yl or pyrrol-3-yl, which are unsubstituted or substituted by 1-2 substituents selected from the group consisting of F, Cl, Br, I, —CN, $(C_2-C_5)$-alkanoyl, $(C_2-C_5)$-alkoxycarbonyl, formyl, carboxyl, —$CF_3$ and methyl;

or

R(1), R(2) and R(3) independently of one another are hydrogen or alkyl having 1, 2, 3 or 4 carbon atoms;

or

R(1), R(2) and R(3) independently of one another are —Q—4-{$(CH_2)_k$—CH(NR(21)R(22))—(C=O)R(20)}-phenyl, —Q—3-{$(CH_2)_k$—CH(NR(21)R(22))—(C=O)R(20)}-phenyl or —Q—2-{$(CH_2)_k$—CH(NR(21)R(22))—(C=O)R(20)}-phenyl, where the phenyl in each case is unsubstituted or substituted by 1-2 substituents selected from the group consisting of F, Cl, —$CF_3$, methyl, hydroxyl, methoxy and —NR(35)R(36); R(35) and R(36) independently of one another are hydrogen or —$CH_3$;

Q is a bond, oxygen, —S— or —NR(18);

R(18) is hydrogen or —$(C_1-C_4)$-alkyl;

R(21) and R(22) independently of one another are hydrogen, —$(C_1-C_5)$-alkyl, —$(C_1-C_5)$-alkanoyl, —$(C_1-C_5)$-alkoxycarbonyl, benzyl or benzyloxycarbonyl;

or

R(21) is trityl;

R(20) is —OR(23) or —NR(23)R(24); R(23) and R(24) independently of one another are hydrogen, —$(C_1-C_4)$-alkyl or benzyl;

k is zero, 1 or 2;

or

R(1), R(2) and R(3) independently of one another are $(C_1-C_9)$-heteroaryl, which is linked via C or N and which is unsubstituted or substituted by a substituent selected from the group consisting of F, Cl, $CF_3$, $CH_3$, methoxy and dimethylamino;

or

R(1), R(2) and R(3) are —SR(25), —OR(25), —NR(25)R(26), —CR(25)R(26)R(27); R(25) is —$C_fH_{2f}$—$(C_1-C_9)$-heteroaryl, which is unsubstituted or substituted by a substituent selected from the group consisting of F, Cl, $CF_3$, $CH_3$, methoxy, dimethylamino;

f is zero, 1 or 2;

R(26) and R(27) independently of one another are defined as R(25) or are hydrogen or methyl;

or

R(1), R(2) and R(3) independently of one another are $(C_1-C_9)$-heteroaryl N-oxide, which is linked via C or N and which is unsubstituted or substituted by 1-2 substituents selected from the group consisting of F, Cl, $CF_3$, $CH_3$, methoxy, hydroxyl, amino, methylamino and dimethylamino;

or

R(1), R(2) and R(3) independently of one another are —SR(28), —OR(28), —NR(28)R(29) or —CR(28)R(29)R(30);

R(28) is —$C_gH_{2g}$—$(C_1-C_9)$-heteroaryl N-oxide, which is unsubstituted or substituted by 1-2 substituents selected from the group consisting of F, Cl, $CF_3$, $CH_3$, methoxy, hydroxyl, amino, methylamino and dimethylamino;

g is zero or 1;

R(29) and R(30) independently of one another are defined as R(28) or are hydrogen or methyl;

or

R(1), R(2) and R(3) independently of one another are hydrogen, F, Cl, $CF_3$, R(31)$SO_2$—, R(32)R(33)N—CO—, R(34)—CO— or R(45)R(46)N—$SO_2$; R(31) and R(34) independently of one another are methyl or —$CF_3$; R(32), R(33), R(45) and R(46) independently of one another are hydrogen or methyl;

or

R(1), R(2) and R(3) independently of one another are R(51)—A—G—D—; R(51) is —NR(52)R(53), an amidino group R(52)R(53)N—C{=N-R(54)}— or a guanidino group R(52)R(53)N-C{=N—R(54)}—NR (55)—; R(52), R(53), R(54) and R(55) independently of one another are hydrogen or alkyl having 1, 2, 3 or 4 carbon atoms;

or

R(52) and R(53) are a group $C_\alpha H_{2\alpha}$;
α is 4, 5, 6 or 7;
where if α=5, 6 or 7 a carbon atom of the group $C_\alpha H_{2\alpha}$ can be replaced by a heteroatom group O, $SO_d$ or NR(56);

or

R(53) and R(54) are a group $C_\gamma H_{2\gamma}$;
γ is 2, 3, 4 or 5;
where if γ=3, 4 or 5 a carbon atom of the group $C_\gamma H_{2\gamma}$ can be replaced by a heteroatom group O, $SO_d$ or NR(56);
d is zero or 2;
R(56) is hydrogen or methyl;

or

R(51) is imidazolyl, pyridyl, quinolinyl or isoquinolinyl;
A is a group $C_e H_{2e}$;
e is zero, 1, 2, 3, 4 or 5;
where in the group $C_e H_{2e}$ a carbon atom can be replaced by one of the groups —O—, —CO—, —CH{OR(57)}—, —SO$_r$—, —NR(57)—, —NR (57)—CO—, —NR(57)—CO—NH—, —NR(57)—CO—NH—SO$_2$— or —NR(57)—SO$_2$—;
r is zero or 2;
G is a phenylene radical

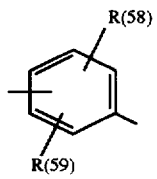

R(58) and R(59) independently of one another are hydrogen, methyl, F, Cl, CF$_3$ or —SO$_2$—R(60); R(60) is methyl or NR(61)R(62); R(61) and R(62) independently of one another are hydrogen or methyl;

D is —C$_v$H$_{2v}$—E$_w$—;
v is zero, 1, 2, 3 or 4;
E is —O—, —CO—, —CH{OR(63)}—, —SO$_{aa}$— or —NR(63)—;
w is zero or 1;
aa is zero or 2
R(63) is hydrogen or methyl;

or

R(2) is —CF$_2$R(64), —CF{R(65)}{R(66)}, —CF(CF$_3$){R(65)}, —C(CF$_3$)=CR(65)R(66); R(64) is alkyl having 1, 2, 3 or 4 carbon atoms or cycloalkyl having 3, 4, 5, 6 or 7 carbon atoms; R(65) and R(66) independently of one another are hydrogen or alkyl having 1, 2, 3 or 4 carbon atoms;

or

R(1), R(2) and R(3) independently of one another are —OR(67) or —NR(67)R(68); R(67) and R(68) independently of one another are hydrogen or alkyl having 1,2 or 3 carbon atoms;

or

R(67) and R(68) together are 4, 5 or 6 methylene groups, of which one CH$_2$ group can be replaced by oxygen, —S—, SO$_2$, —NH— or —NCH$_3$;

R(4) and R(5) independently of one another are hydrogen, alkyl having 1, 2 or 3 carbon atoms, F, Cl, —OR(69), —NR(70)R(71) or —CF$_3$; R(69), R(70) and R(71) independently of one another are hydrogen or methyl;

R(6) and R(7) independently of one another are hydrogen or methyl.

3. A compound of the formula I as claimed in claim 1, wherein:

R(1), R(2) and R(3) independently of one another are —O—{4—R(8)-phenyl}, the phenyl in each case is unsubstituted or substituted by a substituent from the group consisting of F, Cl, —CF$_3$, methyl and methoxy;

R(8) is SO$_a${NR(98)}$_b$NR(99)R(10);
a is 1 or 2;
b is 0 or 1;
a+b=2;
R(98) is hydrogen or alkyl having 1, 2, 3 or 4 carbon atoms;

R(99) and R(10) independently of one another are hydrogen, alkyl having 1 or 2 carbon atoms, benzyl, —(C$_2$–C$_3$)-alkylene—NR(11)R(12), (C$_2$–C$_3$)-alkylene—NR(13)—(C$_2$–C$_3$)-alkylene—NR(37)R(38) or (C$_0$–C$_2$)-alkylene-CR(39)R(40)—CR(41)R(42) (C$_0$–C$_2$)-alkylene—NR(43)R(44); R(11), R(12), R(13), R(37), R(38), R(43) and R(44) independently of one another are hydrogen, methyl or ethyl; R(39), R(40), R(41) and R(42) independently of one another are hydrogen, alkyl having 1, 2, 3 or 4 carbon atoms or benzyl, where the phenyl is unsubstituted or substituted by a substituent selected from the group consisting of F, Cl, —CF$_3$, methyl and methoxy;

or

R(99) and R(10) together are 4, 5 or 6 methylene groups, of which one CH$_2$ group can be replaced by —NH— or —NCH$_3$.

or

R(8) is SO$_a${NR(98)}$_b$NR(95)—C{=N—R(94)}—NR (93)R(92); R(95) is hydrogen; R(92), R(93) and R(94) independently of one another are hydrogen or alkyl having 1, 2, 3 or 4 carbon atoms;

or

R(1), R(2) and R(3) independently of one another are pyrrol-1-yl, which is unsubstituted or substituted by 1–2 substituents selected from the group consisting of F, Cl, Br, I, —CN, acetyl, (C$_2$–C$_5$)-alkoxycarbonyl, —CF$_3$ and methyl;

or

R(1), R(2) and R(3) independently of one another are hydrogen or alkyl having 1, 2, 3 or 4 carbon atoms;

or

R(1), R(2) and R(3) independently of one another are —Q—4—{(CH$_2$)$_k$—CH(NR(21)R(22))—(C=O)R (20)}-phenyl, where the phenyl in each case is unsubstituted or substituted by a substituent selected from the group consisting of F, Cl, —CF$_3$, methyl, hydroxyl and methoxy;

Q is a bond or oxygen;

R(21), R(22) independently of one another are hydrogen, methyl, —(C$_1$–C$_5$)-alkanoyl, —(C$_1$–C$_5$)-alkoxycarbonyl, benzyl or benzyloxycarbonyl;

R(20) is —OR(23) or —NR(23)R(24); R(23), R(24) independently of one another are hydrogen, —(C$_1$–C$_4$)-alkyl or benzyl;

k is zero, 1 or 2;

or

R(1), R(2) and R(3) independently of one another are imidazolyl, which is linked via C or N and which is unsubstituted or substituted by a substituent selected from the group consisting of F, Cl, CF$_3$, CH$_3$ and methoxy;

or

R(1), R(2) and R(3) are —SR(25), —OR(25), —NR(25)R(26), —CR(25)R(26)R(27); R(25) is —(C$_1$–C$_9$)-heteroaryl, which is unsubstituted or substituted by a substituent selected from the group consisting of F, Cl, CF$_3$, CH$_3$ and methoxy;

R(26), R(27) independently of one another are hydrogen or methyl;

or

R(1), R(2) and R(3) independently of one another are —SR(28), —OR(28), —NR(28)R(29) or —CR(28)R(29)R(30);

R(28) is —(C$_1$–C$_9$)-heteroaryl N-oxide, which is unsubstituted or substituted by a substituent selected from the group consisting of F, Cl, CF$_3$, CH$_3$ and methoxy;

R(29) and R(30) independently of one another are hydrogen or methyl;

or

R(1), R(2) and R(3) independently of one another are hydrogen, F, Cl, CF$_3$, R(31)SO$_2$—, R(32)R(33)N—CO—, R(34)—CO— or R(45)R(46)N—SO$_2$; R(31) and R(34) independently of one another are methyl or —CF$_3$; R(32), R(33), R(45) and R(46) independently of one another are hydrogen or methyl;

or

R(2) is R(51)—A—G—D—; R(51) is —NR(52)R(53), an amidino group R(52)R(53)N—C{=N—R(54)}— or a guanidino group R(52)R(53)N—C{=N—R(54)}—NR(55)—; R(52), R(53), R(54) and R(55) independently of one another are hydrogen or alkyl having 1, 2, 3 or 4 carbon atoms;

or

R(52) and R(53) are a group C$_\alpha$H$_{2\alpha}$;

α is 4, 5, 6 or 7;

where if α=5, 6 or 7 a carbon atom of the group C$_\alpha$H$_{2\alpha}$ can be replaced by a heteroatom group O, SO$_d$ or NR(56);

or

R(53) and R(54) are a group C$_\gamma$H$_{2\gamma}$;

γ is 2, 3, 4 or 5;

where if γ=3, 4 or 5 a carbon atom of the group C$_\gamma$H$_{2\gamma}$ can be replaced by a heteroatom group O, SO$_d$ or NR(56);

d is zero or 2;

R(56) is hydrogen or methyl;

or

R(51) is imidazolyl, pyridyl, quinolinyl or isoquinolinyl;

A is C$_e$H$_{2e}$;

e is zero, 1, 2, 3, 4 or 5;

where in the group C$_e$H$_{2e}$ a carbon atom can be replaced by one of the groups —O—, —CO—, —CH{OR(57)}—, —SO$_r$—, —NR(57)—, —NR(57)—CO—, —NR(57)—CO—NH—, —NR(57)—CO—NH—SO$_2$— or —NR(57)—SO$_2$—;

r is zero or 2;

G is a phenylene radical

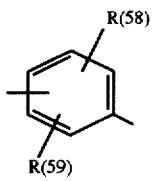

R(58) and R(59) independently of one another are hydrogen, methyl, F, Cl, CF$_3$ or —SO$_2$—R(60); R(60) is methyl or NR(61)R(62); R(61) and R(62) independently of one another are hydrogen or methyl;

D is —C$_v$H$_{2v}$—E$_w$—;

v is zero, 1, 2, 3 or 4;

E is —O—, —CO—, —CH{OR(63)}—, —SO$_{aa}$— or —NR(63)—;

w is zero or 1;

aa is zero or 2

R(63) is hydrogen or methyl, or

R(2) is —CF$_2$R(64), —CF{R(65)}{R(66)}, —CF(CF$_3$){R(65)}, —C(CF$_3$)=CR(65)R(66); R(64) is alkyl having 1, 2, 3 or 4 carbon atoms or cycloalkyl having 3, 4, 5, 6 or 7 carbon atoms; R(65) and R(66) independently of one another are hydrogen or alkyl having 1, 2, 3 or 4 carbon atoms;

or

R(1), R(2) and R(3) independently of one another are —OR(67) or —NR(67)R(68); R(67) and R(68) independently of one another are hydrogen or alkyl having 1, 2 or 3 carbon atoms;

or

R(67) and R(68) together are 4, 5 or 6 methylene groups, of which one CH$_2$ group can be replaced by oxygen, —S—, SO$_2$, —NH— or —NCH$_3$;

R(4) and R(5) independently of one another are hydrogen, alkyl having 1, 2 or 3 carbon atoms, F, Cl, —OR(69), —NR(70)R(71) or —CF$_3$ R(69), R(70) and R(71) independently of one another are hydrogen or methyl;

R(6) and R(7) independently of one another are hydrogen or methyl.

4. A compound of the formula I as claimed in claim 1, wherein:

R(2) is —O—{4-R(8)-phenyl},

R(8) is SO$_a${NR(98)}$_b$NR(99)R(10);

a is 1 or 2;

b is 0 or 1;

a+b=2;

R(98) is hydrogen or alkyl having 1, 2, 3 or 4 carbon atoms;

R(99) and R(10) independently of one another are hydrogen, alkyl having 1 or 2 carbon atoms, —(C$_2$–C$_3$)-alkylene—NR(11)R(12);

R(11) and R(12) independently of one another are hydrogen, methyl or ethyl;

or

R(99) and R(10) together are 5 or 6 methylene groups, of which one CH$_2$ group can be replaced by —NH— or —N—CH$_3$;

or

R(8) is SO$_a${NR(98)}$_b$NR(95)—C{=N—R(94)}—NR(93)R(92); R(95) is hydrogen; R(92), R(93) and R(94) independently of one another are hydrogen or alkyl having 1, 2, 3 or 4 carbon atoms;

or

R(1) is pyrrol-1-yl, which is unsubstituted or substituted by 1-2 substituents selected from the group consisting of F, Cl, Br, I, —CN, acetyl, —CF₃ and methyl;

or

R(1), R(2) and R(3) independently of one another are hydrogen or alkyl having 1, 2, 3 or 4 carbon atoms;

or

R(2) is —O—4—{CH₂—CH(NR(21)R(22))—(C=O)R(20)}-phenyl,

R(21) and R(22) independently of one another are hydrogen, methyl, —(C₁-C₅)-alkanoyl, —(C₁-C₅)-alkoxycarbonyl, benzyl, benzyloxycarbonyl;

R(20) is —OR(23) or —NR(23)R(24); R(23) and R(24) independently of one another are hydrogen or —(C₁-C₄)-alkyl;

or

R(2) is imidazolyl, which is linked via C or N;

or

R(2) is —SR(25) or —OR(25); R(25) is pyridyl, quinolinyl or isoquinolinyl, which is unsubstituted or substituted by a substituent selected from the group consisting of F, Cl, CF₃, CH₃ and methoxy;

or

R(2) is —SR(28) or —OR(28); R(28) is pyridyl N-oxide, quinolinyl N-oxide or isoquinolinyl N-oxide, which is unsubstituted or substituted by a substituent selected from the group consisting of F, Cl, CF₃, CH₃ and methoxy;

or

R(1) is hydrogen, F, Cl, CF₃, R(31)SO₂—, or R(45)R(46)N—SO₂; R(31) is methyl or —CF₃, R(45) and R(46) independently of one another are hydrogen or methyl;

or

R(2) is R(51)—A—G—O—; R(51) is —NR(52)R(53); R(52) and R(53) independently of one another are hydrogen or alkyl having 1 or 2 carbon atoms;

or

R(52) and R(53) are $C_\alpha H_{2\alpha}$;
α is 5 or 6;
where a carbon atom of the group $C_a H_{2\alpha}$ can be replaced by NR(56);
R(56) is hydrogen or methyl;

or

R(51) is imidazolyl, pyridyl, quinolinyl or isoquinolinyl;
A is $C_e H_{2e}$;
e is zero, 1, 2 or 3;
where in the group $C_e H_{2e}$ a carbon atom can be replaced by one of the groups —O—, —CH{OR(57)}—, —SO_r—, —NR(57)—, or —NR(57)—SO₂—;
r is zero or 2;
G is a phenylene radical

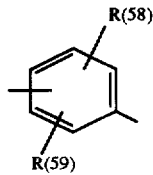

or

R(2) is —CF₂R(64), —CF{R(65)}{R(66)}, —CF(CF₃){R(65)}, —C(CF₃)=CR(65)R(66);

R(64) is alkyl having 1, 2, 3 or 4 carbon atoms or cycloalkyl having 5 or 6 carbon atoms;

R(65) and R(66) independently of one another are hydrogen or alkyl having 1, 2, 3 or 4 carbon atoms;

or

R(1), R(2) and R(3) independently of one another are —OR(67) or —NR(67)R(68);

R(67) and R(68) independently of one another are hydrogen, methyl or ethyl;

or

R(67) and R(68) together are 4-5 methylene groups, of which one CH₂ group can be replaced by oxygen, —NH— or —NCH₃;

R(4) and R(5) independently of one another are hydrogen, alkyl having 1, 2 or 3 carbon atoms, F, Cl, or —CF₃;

R(6) and R(7) independently of one another are hydrogen or methyl.

5. A compound of the formula I as claimed in claim 1, selected from the group consisting of 4-(3-pyridyloxy)-3-trifluoromethylbenzyloxycarbonylguanidine dihydrochloride, 4-(6-quinaldinyloxy)-3-methylsulfonylbenzyloxycarbonylguanidine dihydrochloride, 4-(6-quinaldinyloxy)-3-trifluoromethylbenzyloxycarbonylguanidine dihydrochloride, 4-isopropyl-3-methylsulfonylbenzyloxycarbonylguanidine hydrochloride, 3-isopropylbenzyloxycarbonylguanidine hydrochloride, 2-chloro-5-trifluoromethylbenzyloxycarbonylguanidine hydrochloride, 4-(6-quinolinyloxy)-3-methylsulfonylbenzyloxycarbonylguanidine dihydrochloride, 3,5-difluorobenzyloxycarbonylguanidine hydrochloride, 2,5-difluorobenzyloxycarbonylguanidine hydrochloride, 2,3,6-trifluorobenzyloxycarbonylguanidine hydrochloride, 4-isopropyl3-methylsulfonylbenzyloxycarbonylguanidine hydrochloride, 3-methylsulfonyl-4-phenoxybenzyloxycarbonylguanidine methanesulfonate, 2-chloro-5-trifluoromethylbenzyloxycarbonylguanidine hydrochloride, 3-isopropylbenzyloxycarbonylguanidine hydrochloride, 4-(6-quinolyloxy)-3-methylsulfonylbenzyloxycarbonylguanidine hydrochloride and 3-trifluoromethyl-4-methoxybenzyloxycarbonylguanidine hydrochloride.

6. A process for preparing a compound of the formula I as claimed in claim 1, which comprises reacting with a guanidine a compound of the formula IV

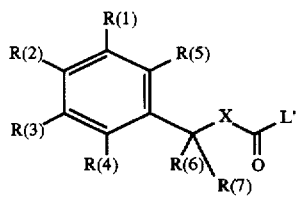

in which R(1) to R(7) and X have the meanings given in claim 1, and in which L' is chlorine, ethoxy, isobutoxy, benzotriazol-1-oxy or 1-imidazolyl.

7. A method for the treatment of arrhythmias comprising administering an effective amount of a compound of the formula I as claimed in claim 1.

8. A method for treating arrhythmias, which comprises treating an effective amount of a compound I as claimed in claim 1 with the customary additives and administering in a suitable presentation form.

9. A method for the treatment or prophylaxis of cardiac infarct comprising administering an effective amount of a compound of the formula I as claimed in claim 1.

10. A method for the treatment or prophylaxis of angina pectoris comprising administering an effective amount of a compound of the formula I as claimed in claim 1.

11. A method for the treatment or prophylaxis of ischemic conditions of the heart comprising administering an effective amount of a compound of the formula I as claimed in claim 1.

12. A method for the treatment or prophylaxis of ischemic conditions of the peripheral and central nervous system and of stroke comprising administering an effective amount of a compound of the formula I as claimed in claim 1.

13. A method for the treatment or prophylaxis of ischemic conditions of peripheral organs and limbs comprising administering an effective amount of a compound of the formula I as claimed in claim 1.

14. A method for the treatment of states of shock comprising administering an effective amount of a compound of the formula I as claimed in claim 1.

15. A method for protecting organs during surgical operations or organ transplants comprising administering an effective amount of a compound of the formula I as claimed in claim 1.

16. A method for the preservation and storage of transplants for surgical measures comprising administering an effective amount of a compound of the formula I as claimed in claim 1.

17. A method for the treatment of diseases in which cell proliferation is a primary or secondary cause comprising administering an effective amount of a compound of the formula I as claimed in claim 1 as an antiatherosclerotic agent, agent against diabetic late complications, carcinomatous disorders, pulmonary fibrosis, hepatic fibrosis, renal fibrosis, or prostate hyperplasia.

18. A method for the diagnosis of hypertension and proliferative disorders comprising administering a compound of the formula I as claimed in claim 1 as a diagnostic agent for the inhibition of a cellular $Na^+/H^+$ exchanger.

19. A pharmaceutical composition comprising an effective amount of a compound I as claimed in one claim 1.

* * * * *